(12) United States Patent
Baird et al.

(10) Patent No.: US 7,927,789 B1
(45) Date of Patent: Apr. 19, 2011

(54) SELF-REFERENCING BIODETECTION METHOD AND PATTERNED BIOASSAYS

(75) Inventors: Cheryl Baird, Cambridge, MA (US); Brian T. Cunningham, Champaign, IL (US); Peter Li, Andover, MA (US)

(73) Assignee: SRU Biosystems, Inc., Woburn, MA (US)

( * ) Notice: Subject to any disclaimer, the term of this patent is extended or adjusted under 35 U.S.C. 154(b) by 206 days.

(21) Appl. No.: 12/426,552

(22) Filed: Apr. 20, 2009

Related U.S. Application Data

(62) Division of application No. 11/943,064, filed on Nov. 20, 2007, now Pat. No. 7,534,578, which is a division of application No. 10/727,680, filed on Dec. 4, 2003, now Pat. No. 7,309,614.

(60) Provisional application No. 60/430,911, filed on Dec. 4, 2002.

(51) Int. Cl.
*G01N 33/551* (2006.01)

(52) U.S. Cl. ...... 435/4; 422/82.11; 435/288.7; 435/808; 436/164; 436/524; 436/528

(58) Field of Classification Search ........................ None
See application file for complete search history.

(56) References Cited

U.S. PATENT DOCUMENTS

| | | |
|---|---|---|
| 3,916,182 A | 10/1975 | Dabby et al. |
| 4,009,933 A | 3/1977 | Firester |
| 4,536,608 A | 8/1985 | Sheng et al. |
| 4,576,850 A | 3/1986 | Martens |
| 4,668,558 A | 5/1987 | Barber |
| 4,857,273 A | 8/1989 | Stewart |
| 4,876,208 A | 10/1989 | Gustafson et al. |
| 4,882,288 A | 11/1989 | North et al. |
| 4,931,384 A | 6/1990 | Layton et al. |
| 4,958,895 A | 9/1990 | Wells et al. |
| 4,992,385 A | 2/1991 | Godfrey |
| 4,999,234 A | 3/1991 | Cowan |
| 5,118,608 A | 6/1992 | Layton et al. |
| 5,156,785 A | 10/1992 | Zdrahala |
| 5,170,448 A | 12/1992 | Ackley et al. |
| 5,175,030 A | 12/1992 | Lu et al. |
| 5,210,404 A | 5/1993 | Cush et al. |
| 5,229,614 A | 7/1993 | Andersson et al. |
| 5,242,828 A | 9/1993 | Bergstrom et al. |
| 5,268,782 A | 12/1993 | Wenz et al. |
| 5,337,183 A | 8/1994 | Rosenblatt |
| 5,413,884 A | 5/1995 | Koch et al. |
| 5,442,169 A | 8/1995 | Kunz |

(Continued)

FOREIGN PATENT DOCUMENTS

EP 0 112 721 7/1984

(Continued)

OTHER PUBLICATIONS

U.S. Appl. No. 60/244,312, filed Oct. 30, 2000, Cunningham et al.

(Continued)

*Primary Examiner* — Christopher L Chin
(74) *Attorney, Agent, or Firm* — McDonnell Boehnen Hulbert & Berghoff LLP

(57) ABSTRACT

The invention relates to compositions and methods for detecting biomolecular interactions. The detection can occur without the use of labels and can be done in a high-throughput manner. The invention further relates to self-referencing colorimetric resonant optical biosensors and optical devices.

5 Claims, 23 Drawing Sheets

Self-referencing Colormetric Resonant Optical Biosensor

U.S. PATENT DOCUMENTS

| | | |
|---|---|---|
| 5,455,178 A | 10/1995 | Fattinger |
| 5,475,780 A | 12/1995 | Mizrahi |
| 5,478,527 A | 12/1995 | Gustafson et al. |
| 5,478,756 A | 12/1995 | Gizeli et al. |
| 5,492,840 A | 2/1996 | Malmqvist et al. |
| 5,496,701 A | 3/1996 | Pollard-Knight |
| 5,559,338 A | 9/1996 | Elliott et al. |
| 5,598,267 A | 1/1997 | Sambles et al. |
| 5,598,300 A | 1/1997 | Magnusson et al. |
| 5,606,170 A | 2/1997 | Saaski et al. |
| 5,615,052 A | 3/1997 | Doggett |
| 5,666,197 A | 9/1997 | Guerra |
| 5,690,894 A | 11/1997 | Pinkel et al. |
| 5,691,846 A | 11/1997 | Benson, Jr. et al. |
| 5,732,173 A | 3/1998 | Bylander et al. |
| 5,738,825 A | 4/1998 | Rudigier et al. |
| 5,771,328 A | 6/1998 | Wortman et al. |
| 5,792,411 A | 8/1998 | Morris et al. |
| 5,801,390 A | 9/1998 | Shiraishi |
| 5,804,453 A | 9/1998 | Chen |
| 5,814,524 A | 9/1998 | Walt et al. |
| 5,846,843 A | 12/1998 | Simon |
| 5,864,641 A | 1/1999 | Murphy et al. |
| 5,925,878 A | 7/1999 | Challener |
| 5,955,378 A | 9/1999 | Challener |
| 5,986,762 A | 11/1999 | Challener |
| 5,991,480 A | 11/1999 | Kunz et al. |
| 5,994,150 A | 11/1999 | Challener et al. |
| 6,035,089 A | 3/2000 | Grann et al. |
| 6,052,213 A | 4/2000 | Burt et al. |
| 6,076,248 A | 6/2000 | Hoopman et al. |
| 6,088,505 A | 7/2000 | Hobbs |
| 6,100,991 A | 8/2000 | Challener |
| 6,146,593 A | 11/2000 | Pinkel et al. |
| 6,185,019 B1 | 2/2001 | Hobbs et al. |
| 6,218,194 B1 | 4/2001 | Lyndin et al. |
| 6,277,653 B1 | 8/2001 | Challener |
| 6,316,153 B1 | 11/2001 | Goodman et al. |
| 6,320,991 B1 | 11/2001 | Challener et al. |
| RE37,473 E | 12/2001 | Challener |
| 6,338,968 B1 | 1/2002 | Hefti |
| 6,340,598 B1 | 1/2002 | Herron et al. |
| 6,346,376 B1 | 2/2002 | Sigrist et al. |
| 6,377,721 B1 | 4/2002 | Walt et al. |
| 6,395,558 B1 | 5/2002 | Duveneck et al. |
| 6,404,554 B1 | 6/2002 | Lee et al. |
| 6,587,276 B2 | 7/2003 | Daniell |
| 6,771,376 B2 | 8/2004 | Budach et al. |
| 6,867,869 B2 | 3/2005 | Budach et al. |
| 6,870,630 B2 | 3/2005 | Budach et al. |
| 6,951,715 B2 | 10/2005 | Cunningham et al. |
| 6,990,259 B2 | 1/2006 | Cunningham |
| 7,023,544 B2 | 4/2006 | Cunningham et al. |
| 7,064,844 B2 | 6/2006 | Budach et al. |
| 7,070,987 B2 | 7/2006 | Cunningham et al. |
| 7,094,595 B2 | 8/2006 | Cunningham et al. |
| 7,101,660 B2 | 9/2006 | Cunningham et al. |
| 7,118,710 B2 | 10/2006 | Cunningham |
| 7,142,296 B2 | 11/2006 | Cunningham et al. |
| 7,148,964 B2 | 12/2006 | Cunningham et al. |
| 7,153,702 B2 | 12/2006 | Lin et al. |
| 7,158,230 B2 | 1/2007 | Cunningham et al. |
| 7,162,125 B1 | 1/2007 | Schulz |
| 7,170,599 B2 | 1/2007 | Cunningham et al. |
| 7,175,980 B2 | 2/2007 | Qiu et al. |
| 7,197,198 B2 | 3/2007 | Schulz |
| 7,202,076 B2 | 4/2007 | Cunningham et al. |
| 7,217,574 B2 | 5/2007 | Pien et al. |
| 7,264,973 B2 | 9/2007 | Lin et al. |
| 7,292,336 B2 | 11/2007 | Cunningham et al. |
| 7,298,477 B1 | 11/2007 | Cunningham et al. |
| 7,309,614 B1 | 12/2007 | Baird |
| 7,396,675 B2 | 7/2008 | Pawlak et al. |
| 7,479,404 B2 | 1/2009 | Cunningham |
| 7,483,127 B1 | 1/2009 | Li |
| 7,497,992 B2 | 3/2009 | Cunningham |
| 7,521,769 B2 | 4/2009 | Cunningham |
| 7,524,625 B2 | 4/2009 | Madison |
| 7,534,578 B1 | 5/2009 | Baird |
| 7,620,276 B2 | 11/2009 | Schulz |
| 7,628,085 B2 | 12/2009 | Laing et al. |
| 7,742,662 B2 | 6/2010 | Cunningham |
| 7,756,365 B2 | 7/2010 | Cunningham |
| 7,790,406 B2 | 9/2010 | Cunningham |
| 2002/0018610 A1 | 2/2002 | Challener et al. |
| 2002/0028480 A1 | 3/2002 | Maher |
| 2002/0127565 A1 | 9/2002 | Cunningham et al. |
| 2003/0017581 A1 | 1/2003 | Li |
| 2003/0027327 A1 | 2/2003 | Cunningham et al. |
| 2003/0027328 A1 | 2/2003 | Cunningham et al. |
| 2003/0092075 A1 | 5/2003 | Pepper |
| 2003/0104479 A1 | 6/2003 | Bright |
| 2003/0113766 A1 | 6/2003 | Pepper |
| 2004/0132172 A1 | 1/2004 | Cunningham |
| 2005/0214803 A1 | 9/2005 | Wang |
| 2005/0227374 A1 | 10/2005 | Cunningham |
| 2006/0003372 A1 | 1/2006 | Li |
| 2006/0030033 A1 | 2/2006 | Cunningham |
| 2006/0040376 A1 | 2/2006 | Cunningham |
| 2006/0057707 A1 | 3/2006 | Lin et al. |
| 2006/0286663 A1 | 7/2006 | Cunningham |
| 2006/0181705 A1 | 8/2006 | Cunningham |
| 2006/0275825 A1 | 12/2006 | Laing et al. |
| 2006/0281077 A1 | 12/2006 | Cunningham et al. |
| 2007/0041012 A1 | 2/2007 | Cunningham et al. |
| 2007/0054339 A1 | 3/2007 | Lin et al. |
| 2007/0141231 A1 | 6/2007 | Cunningham et al. |
| 2007/0172894 A1 | 7/2007 | Genick |
| 2008/0213910 A1 | 9/2008 | Jogikalmath |
| 2008/0219615 A1 | 9/2008 | Cunningham |
| 2008/0219892 A1 | 9/2008 | Cunningham |
| 2008/0240543 A1 | 10/2008 | Budach |
| 2008/0299673 A1 | 12/2008 | Laing et al. |
| 2009/0017488 A1 | 1/2009 | Laing et al. |
| 2009/0130703 A1 | 5/2009 | Wagner |
| 2009/0137422 A1 | 5/2009 | Laing |
| 2009/0148955 A1 | 6/2009 | Cunningham |
| 2009/0176658 A1 | 7/2009 | Madison |
| 2009/0179637 A1 | 7/2009 | Cunningham |
| 2009/0192049 A1 | 7/2009 | Laing et al. |
| 2009/0264314 A1 | 10/2009 | Cunningham |
| 2009/0269244 A1 | 10/2009 | Cunningham |
| 2009/0282931 A1 | 11/2009 | Laing |
| 2009/0305304 A1 | 12/2009 | Laing |
| 2010/0003743 A1 | 1/2010 | Schulz |
| 2010/0008826 A1 | 1/2010 | Schulz |
| 2010/0015721 A1 | 1/2010 | Laing |
| 2010/0043571 A1 | 2/2010 | Laing |
| 2010/0143959 A1 | 6/2010 | Cunningham |
| 2010/0195099 A1 | 8/2010 | Rockney |
| 2010/0196925 A1 | 8/2010 | Genick |
| 2010/0202923 A1 | 8/2010 | Cunningham |
| 2010/0227769 A1 | 9/2010 | Schulz |
| 2010/0231907 A1 | 9/2010 | Pien |

FOREIGN PATENT DOCUMENTS

| | | |
|---|---|---|
| EP | 0 517 777 | 5/1996 |
| EP | 0 660 924 | 9/1999 |
| EP | 1031828 | 8/2000 |
| EP | 1085315 | 3/2001 |
| GB | 2 227 089 | 7/1990 |
| WO | WO 84/02578 | 7/1984 |
| WO | WO 90/00831 | 7/1990 |
| WO | WO 91/13339 | 9/1991 |
| WO | WO 92/21768 | 12/1992 |
| WO | WO 93/14392 | 7/1993 |
| WO | WO 95/03538 | 2/1995 |
| WO | WO 98/57200 | 12/1998 |
| WO | WO 99/09392 | 2/1999 |
| WO | WO 99/09396 | 2/1999 |
| WO | WO 99/66330 | 12/1999 |
| WO | WO 00/23793 | 4/2000 |
| WO | WO 01/02839 | 1/2001 |
| WO | WO 01/04697 | 1/2001 |
| WO | WO 01/92870 | 12/2001 |
| WO | 2010005600 | 1/2010 |

OTHER PUBLICATIONS

U.S. Appl. No. 60/283,314, filed Apr. 12, 2001, Cunningham et al.
U.S. Appl. No. 60/303,028, filed Jul. 3, 2001, Cunningham et al.
U.S. Appl. No. 60/430,911, filed Dec. 4, 2002, Baird et al.
Brecht, et al., "Optical probes and transducers", *Biosensors & Bioelectronics* vol. 10, pp. 923-936 (1995).
Cerac, Technical publications: Tantalum Oxide, Ta2O5 for Optical Coating, 2000, Cerac, Inc.
Challener, et al., "A multilayer grating-based evanescent wave sensing technique", *Elsevier Science B.V.*, pp. 42-46 (2000).
Cowan, "Aztec surface-relief volume diffractive structure", *J. Opt. Soc. Am.*, vol. 7, No. 8, pp. 1529-1544 (1990).
Cowan, "Holographic honeycomb microlens", *Optical Engineering*, vol. 24, No. 5, pp. 796-802 (1985).
Cowan, "The Recording and large Scale Replication of Crossed Holographic Grating Arrays using Multiple Beam Interferometry", *SPIE* vol. 503, pp. 120-129 (1984).
Cowan, et al., "The Recording and Replication of Holographic Micropatterns for the Ordering of Photographic Emulsion Grains in Film Systems", *J. Imaging Sci.*, vol. 31, No. 3, pp. 100-107 (1987).
Cunningham, B. et al., "A Plastic colorimetric resonant optical biosensor for multiparallel detection of label-free biochemical interactions", *Sensors and Actuators* B 85; pp. 219-226 (2002).
Cunningham, B. et al., "Colorimetric resonant reflection as a direct biochemical assay technique", *Sensors and Actuators* B 81; pp. 316-328 (2002).
Cunningham, et al., "Optically Based Energy Transduction", *Techniques in Analytical Chemistry*, pp. 260-295.
deWildt et al., "Antibody arrays for high-throughput screening of antibody antigen interactions", *Nature Biotechnology*, 18, p. 989-994, (2000).
Hobbs, et al., "Automated Interference Lithography Systems for Generation of Sub-Micron Feature Size Patterns", *SPIE*, vol. 3879, pp. 124-135, (1999).
Huber, et al., "Direct optical immunosensing (sensitivity and selectivity)", *Sensors and Actuators* B, 6, pp. 122-126 (1992).
Jenison, et al., "Interference-based detection of nucleic acid targets on optically coated silicon", *Nature Biotechnology*, vol. 19, pp. 62-64 (2001).
Jin, et al., "A biosensor concept based on imaging ellipsometry for visualization of biomolecular interactions", *Analytical Biochemistry*, vol. 232, pp. 69-72 (1995).
Jordan, et al., "Surface Plasmon Resonance Imaging Measurement of Electrostatic Biopolymer Adsorption onto Chemically Modified Gold Surfaces", *Analytical Chemistry*, vol. 69, No. 7, pp. 1449-1456 (1997).
Lin, et al., "A Porous Silicon-Based Optical Interferometric Biosensor", *Science*, vol. 278, pp. 840-843 (1997).
MacBeath, et al., "Printing Proteins as Micorarrays for High-Throughput Function Determination", *Science*, vol. 289, p. 1760-1763 (2000).
Magnusson, et al., "New principle for optical filters", *Appl. Phys. Lett.*, vol. 61, No. 9, pp. 1022-1024 (1992).
Magnusson, et al., "Transmission bandpass guided-mode resonance filters", *Applied Optics*, vol. 34, No. 35, pp. 8106-8109 (1995).
Morhard, et al., "Immobilization of antibodies in micropatterns for cell detection by optical diffraction", *Sensors and Actuators* B 70, pp. 232-242 (2000).
Pandey, A. and Mann, M., "Proteomics to study genes and genomes", *Nature* 15;405(6788):837-46 (2000).
Patel, et al., "Electrically tuned and polarization insensitive Fabry-Perot etalon with a liquid-crystal film", *American Institute of Physics*, vol. 58, No. 22, pp. 2491-2493 (1991).
Patel, et al., "Multi-wavelength Tunable Liquid-Crystal Etalon Filter", *IEEE Photonics Technology Letters*, vol. 3, No. 7, pp. 643-644 (1991).
Patterson, S.D., "Proteomics: the industrialization of protein chemistry", *Current Opinions in Biotechnology*. 11(4):413-8 (2000).
Peng, et al., "Experimental demonstration of resonant anomalies in diffraction from two-dimensional gratings", *Optics Letters* vol. 21, No. 8, pp. 549-551 (1996).
Peng, et al., "Resonant scattering from two-dimensional gratings", *J. Opt. Soc. Am. A.*, vol. 13, No. 5, pp. 993-1005 (1996).
Raguin, et al., "Structured Surfaces Mimic Coating Performance", *Laser Focus World*, pp. 113-117 (1997).
Sigal, et al., "A Self-Assembled Monolayer for the Binding and Study of Histidine-Tagged Proteins by Surface Plasmon Resonance", *Analytical Chemistry*, vol. 68, No. 3, pp. 490-497 (1996).
Wang, et al., "Design of wavelength-grating filters with symmetrical line shapes and low sidebands", *Optical Society of America*, vol. 19, No. 12, 919-921 (1994).
Wang, et al., "Guided-mode resonances in planar dielectric-layer diffraction gratings", *J. Opt. Soc. Am.*, vol. 7, No. 8, pp. 1470-1474 (1990).
Wang, et al., "Theory and applications of guided-mode resonance filter", *Applied Optics*, vol. 32, No. 14, pp. 2606-2613 (1993).
International Search Report for foreign counterpart application PCT/US01/50723, Sep. 17, 2002.
International Search Report for foreign counterpart application PCT/US03/01175, Aug. 18, 2003.
Invitation to Pay Additional Fees in foreign counterpart application PCT/US01/50723, Aug. 30, 2002.
Cunningham, "Acoustic-Wave Devices" *Introduction to Bioanalytical Sensors*, pp. 303-318 John Wiley & Sons (1998).
Montagu, "Galvanometric and Resonant Low-Inertia Scanners", *Optical Scanning* pp. 525-537 (1991).
Anderson et al., "Proteomics: applications in basic and applied biology", *Current Opinion in Biotechnology* vol. 11, pp. 408-412 (2000).
Lenau, Torben, *Material Silicon Nitride*, vol. 97, p. 98 (1996).
U.S. Appl. No. 11/566,818, filed Dec. 5, 2006.
U.S. Appl. No. 11/749,073, filed May 15, 2007.
U.S. Appl. No. 11/828,076, filed Jul. 25, 2007.
Palmer, "Diffraction Gratings, The Crucial Dispersive Component", *Spectroscopy*, 10(2), pp. 14-15 1995.
Yariv, "Coupled-Mode Theory for Guided-Wave Optics", *IEEE Journal of Quantum Electronics*, vol. 9, No. 9, p. 919-933 (1973).
Wang et al., "Resonances of Asymmetric Dielectric Waveguides Containing a Diffraction Grating", IEEE (1990).
Hessel et al., "A New Theory of Wood's Anomalies on Optical Gratings", *Applied Optics*, vol. 4, No. 10, p. 1275-1299 (1965).
Lukosz et al., "Sensitivity of Integrated Optical Grating and prism Couplers as (Bio)chemical Sensors", *Sensors and Actuators*, 15, p. 273-284 (1988).
Neviere et al., "About the Theory of Optical Grating Coupler-Wavelength Systems", *Optics Communications*, vol. 8, No. 2, p. 113-117 (1973).
Gaylord et al., "Analysis and Applications of Optical Diffraction by Gratings", *IEEE*, 73(5):894, p. 894-924 (1985).
Cooper, "Current biosensor technologies in drug discovery", *Drug Discovery World Summer* 2006, pp. 68-82.
Comley, "Label-Free Detection New Biosensors facilitate broader ranger of drug discovery applications", Drug Discovery World winter May 2004, pp. 63-74.
Cunningham, "Colorimetric Resonant Reflection as a Direct Biochemical Assay Technique", IEEE, Annual International Conference on Micro Electro Mechanical Systems, MEMS, 2002, Las Vegas, NV, Jan. 20-24, 2002.
Magnusson et al., "Fiber Endface Bioprobes with high Sensitivity and Spatial Resolution", Grant Proposal dated Aug. 11, 1999.
Norton, "Resonant Grating Structures: Theory, Design and Applications", Doctoral Thesis, The University of Rochester, 1997.
Popov et al., "Theoreticia study of the anomalies of coated dielectric gratings", *Optica Acta*, vol. 33, No. 5, pp. 607-619 (1986).
Shin et al., "Thin-film optical filters with diffractive elements and waveguides", *Opt. Eng.* 37(9):2634-2646 (1998).
Tibuleac et al., "Reflection and transmission guided-mode resonance filters", *J. Opt. Soc. Am. A.*, vol. 14, No. 7, pp. 1617-1626 (1997).
Tibuleac et al., "Diffractive Narrow-Band Transmission Filters Bases on Guided-Mode Resonance Effects in Thin-Film Multilayers", *IEEE Photonics Technology Letters*, vol. 9, No. 4, pp. 464-466 (1997).
Wawro, "Design, Fabrication and Testing of Waveguide Gratings for Spectral Filters, Photonic Antennas and Optical Fiber Sensors", Presentation, University of Texas at Arlington (1999).

Wawro et al., "Novel diffractive structures integrating waveguide-gratings on optical fiber endfaces", Presentation, Graduate Student Research Symposium (1999).

Tibuleac, "Guided-mode resononce reflection and transmission filters in the optical and microwave spectral ranges", Doctoral Dissertation Defense (1999).

Hexagonal Grid Design

US 7,927,789 B1

SELF-REFERENCING BIODETECTION METHOD AND PATTERNED BIOASSAYS

PRIORITY

This application is a divisional application of U.S. Ser. No. 11/943,064, filed Nov. 20, 2007 (now allowed), which is a divisional application of U.S. Ser. No. 10/727,680, filed Dec. 4, 2003 (now U.S. Pat. No. 7,309,614), which claims the benefit of U.S. provisional application Ser. No. 60/430,911, filed Dec. 4, 2002. These applications are herein incorporated by reference in their entirety.

TECHNICAL AREA OF THE INVENTION

The invention relates to methods for detecting biomolecular interactions. The detection can occur without the use of labels and can be done in a high-throughput manner. The invention further relates to self-referencing colorimetric resonant optical biosensors. The invention also relates to optical devices.

BACKGROUND OF THE INVENTION

With the completion of the sequencing of the human genome, one of the next grand challenges of molecular biology will be to understand how the many protein targets encoded by DNA interact with other proteins, small molecule pharmaceutical candidates, and a large host of enzymes and inhibitors. See e.g., Pandey & Mann, "Proteomics to study genes and genomes," Nature, 405, p. 837-846, 2000; Leigh Anderson et al., "Proteomics: applications in basic and applied biology," Current Opinion in Biotechnology, 11, p. 408-412, 2000; Patterson, "Proteomics: the industrialization of protein chemistry," Current Opinion in Biotechnology, 11, p. 413-418, 2000; MacBeath & Schreiber, "Printing Proteins as Microarrays for High-Throughput Function Determination," Science, 289, p. 1760-1763, 2000; De Wildt et al., "Antibody arrays for high-throughput screening of antibody-antigen interactions," Nature Biotechnology, 18, p. 989-994, 2000. To this end, tools that have the ability to simultaneously quantify many different biomolecular interactions with high sensitivity will find application in pharmaceutical discovery, proteomics, and diagnostics. Further, for these tools to find widespread use, they must be simple to use, inexpensive to own and operate, and applicable to a wide range of analytes that can include, for example, polynucleotides, peptides, small proteins, antibodies, and even entire cells.

Biosensors have been developed to detect a variety of biomolecular complexes including oligonucleotides, antibody-antigen interactions, hormone-receptor interactions, and enzyme-substrate interactions. In general, biosensors consist of two components: a highly specific recognition element and a transducer that converts the molecular recognition event into a quantifiable signal. Signal transduction has been accomplished by many methods, including fluorescence, interferometry (Jenison et al., "Interference-based detection of nucleic acid targets on optically coated silicon," Nature Biotechnology, 19, p. 62-65; Lin et al., "A porous silicon-based optical interferometric biosensor," Science, 278, p. 840-843, 1997), and gravimetry (A. Cunningham, Bioanalytical Sensors, John Wiley & Sons (1998)).

Of the optically-based transduction methods, direct methods that do not require labeling of analytes with fluorescent compounds are of interest due to the relative assay simplicity and ability to study the interaction of small molecules and proteins that are not readily labeled. Direct optical methods include surface plasmon resonance (SPR) (Jordan & Corn, "Surface Plasmon Resonance Imaging Measurements of Electrostatic Biopolymer Adsorption onto Chemically Modified Gold Surfaces," Anal. Chem., 69:1449-1456 (1997)), grating couplers (Morhard et al., "Immobilization of antibodies in micropatterns for cell detection by optical diffraction," Sensors and Actuators B, 70, p. 232-242, 2000), ellipsometry (Jin et al., "A biosensor concept based on imaging ellipsometry for visualization of biomolecular interactions," Analytical Biochemistry, 232, p. 69-72, 1995), evanescent wave devices (Huber et al., "Direct optical immunosensing (sensitivity and selectivity)," Sensors and Actuators B, 6, p. 122-126, 1992), and reflectometry (Brecht & Gauglitz, "Optical probes and transducers," Biosensors and Bioelectronics, 10, p. 923-936, 1995). Theoretically predicted detection limits of these detection methods have been determined and experimentally confirmed to be feasible down to diagnostically relevant concentration ranges. However, to date, these methods have yet to yield commercially available high-throughput instruments that can perform high sensitivity assays without any type of label in a format that is readily compatible with the microtiter plate-based or microarray-based infrastructure that is most often used for high-throughput biomolecular interaction analysis. Therefore, there is a need in the art for methods that can achieve these goals.

Furthermore, detection of small molecules with low affinities and low concentrations requires the measurement of signals that are near the noise resolution limit of the above instruments. Working with solutions containing small molecules dissolved in solvents such as glycerol or DMSO regularly generates bulk signal changes that are as large, or larger than the signal generated by the small molecule binding event. While separate reference reactions can be used to compensate for the aberrant signal changes, such compensation tactics reduce the number of usable reaction locations by one half. Thus there existed in the art the need for more accurate and efficient means for subtraction of experimental errors such as, for example, solvent effects.

SUMMARY OF THE INVENTION

The invention provides methods for detecting binding or cleavage of one or more specific binding substances to a self-referencing colorimetric resonant optical biosensor surface, or to their respective binding partners which are immobilized on a surface of a colorimetric resonant optical biosensor. This and other embodiments of the invention are provided by one or more of the embodiments described below.

In one embodiment, a self-referencing colorimetric resonant optical biosensor is provided comprising a liquid holding vessel comprising a colorimetric resonant optical biosensor as a surface, such as a bottom surface, and a fluid-impermeable divider. The fluid-impermeable divider is on the colorimetric resonant optical biosensor surface and separates the liquid holding vessel into two or more assay regions, wherein the fluid-impermeable divider segregates an immobilization volume within each assay region. The fluid-impermeable divider allows a reaction volume to encompass all assay regions in the liquid-holding vessel. One or more specific binding substances can be immobilized on one or more of the assay regions of the self-referencing colorimetric resonant optical biosensor to form one or more reaction regions, and no specific binding substances can be immobilized on one or more of the assay regions to form one or more reference regions. When the biosensor is illuminated a resonant grating effect can be produced on the reflected radiation spectrum, and the depth and period of a grating of the biosensor can be less than a wavelength of the resonant grating effect. A narrow band of optical wavelengths can be reflected from the biosensor when the biosensor is illuminated with a broad band of optical wavelengths. The one or more specific binding substances can be bound to their specific binding partners. The liquid-holding vessel can be selected from the group consisting of a microtiter plate well, a test tube, a Petri dish and a microfluidic channel. The biosensor can comprise two or more liquid-holding vessels.

In yet another embodiment, a self-referencing colorimetric resonant optical biosensor is provided, comprising one or more liquid-holding vessels comprising a colorimetric resonant optical biosensor as a surface, such as a bottom surface. One or more specific binding substances are immobilized on a first portion of the colorimetric resonant optical biosensor of each liquid-holding vessel forming a reaction surface, and no specific binding substances are immobilized on a second portion of the colorimetric resonant optical biosensor of each liquid-holding vessel forming a reference surface. The biosensor can comprise two or more reaction surfaces in each liquid holding vessel and two or more reference surfaces in each liquid holding vessel. When the biosensor is illuminated a resonant grating effect is produced on the reflected radiation spectrum and the depth and period of a grating of the biosensor can be less than a wavelength of the resonant grating effect. A narrow band of optical wavelengths can be reflected from the biosensor when the biosensor is illuminated with a broad band of optical wavelengths. The one or more specific binding substances can be bound to their specific binding partners. The liquid-holding vessel can be selected from the group consisting of a microtiter plate well, a test tube, a Petri dish and a microfluidic channel.

In another embodiment, a method of making a self-referencing colorimetric resonant optical biosensor is provided comprising the steps of (i) immobilizing one or more specific binding substances in an immobilization volume to one or more assay regions of a self-referencing colorimetric resonant optical biosensor, wherein the self-referencing colorimetric resonant optical biosensor comprises one or more liquid holding vessels comprising colorimetric resonant optical biosensors as a surface, and a fluid-impermeable divider, wherein the fluid impermeable divider separates the liquid holding vessels into two or more assay regions, wherein the fluid-impermeable divider segregates an immobilization volume within each assay region, and wherein the fluid-impermeable divider allows a reaction volume to encompass all assay regions in the one or more liquid-holding vessels; and (ii) preserving one or more assay regions as one or more reference regions, wherein the one or more reference regions do not contain immobilized specific binding substances.

In another embodiment, a method of making a self-referencing colorimetric resonant optical biosensor is provided comprising immobilizing one or more specific binding substances on a first portion of a surface of a colorimetric resonant optical biosensor forming a reaction region, wherein a second portion of the colorimetric resonant optical biosensor contains no specific binding substances forming a reference region, wherein the colorimetric resonant optical biosensor comprises a surface of a liquid-holding vessel.

In another embodiment, a method is provided for detecting the binding of one or more specific binding substances to their respective binding partners in a self-referencing colorimetric resonant optical biosensor comprising one or more liquid-holding vessels comprising a colorimetric resonant optical biosensor as a surface. A fluid-impermeable divider forms assay regions. One or more specific binding substances immobilized on one or more of the assay regions to form reaction regions. One or more assay regions do not have immobilized specific binding substance to form reference regions. The method comprises (i) applying one or more specific binding partners in a reaction volume to the liquid-holding vessels; (ii) illuminating the one or more reaction regions and the one or more reference regions with light; (iii) detecting a maxima in reflected wavelength, or a minima in transmitted wavelength of light from the one or more reaction regions and the one or more reference regions; and (iv) comparing the maxima or minima of the one or more reference regions to the maxima or minima from the one or more reaction regions. The binding of one or more specific binding substances to their respective binding partners is detected.

In another embodiment, a method is provided for detecting the binding of one or more specific binding substances to their respective binding partners in a self-referencing colorimetric resonant optical biosensor comprising one or more liquid-holding vessels and comprising a colorimetric resonant optical biosensor as a surface of the liquid-holding vessels. One or more specific binding substances are immobilized on a first portion of the colorimetric resonant optical biosensor to form a reaction surface and no specific binding substances are immobilized on a second portion of the colorimetric resonant optical biosensor of each liquid-holding vessel forming a reference surface. The method comprises (i) applying one or more specific binding partners in a reaction volume to the above one or more liquid holding vessels; (ii) illuminating the reaction surfaces and the reference surfaces with light; (iii) detecting a maxima in reflected wavelength, or a minima in transmitted wavelength of light from the reaction surfaces and the reference surfaces; and (iv) comparing the maxima or minima of the one or more reference surfaces to the maxima or minima from the one or more reaction surfaces. The binding of one or more specific binding substances to their respective binding partners is detected.

In another embodiment, a method is provided for detecting activity of an enzyme in a self-referencing colorimetric resonant optical biosensor comprising one or more liquid-holding vessels comprising a colorimetric resonant optical biosensor as a surface. A fluid-impermeable divider forms assay regions. One or more specific binding substances are immobilized on one or more of the assay regions to form reaction regions and one or more assay regions do not have immobilized specific binding substances to form reference regions. The method comprises (i) applying one or more enzymes in a reaction volume to the one or more liquid holding vessels; (ii) illuminating the one or more reaction regions and the one or more reference regions with light; (iii) detecting a maxima in reflected wavelength, or a minima in transmitted wavelength of light from the one or more reaction regions and the one or more reference regions; and (iv) comparing the maxima or minima of the one or more reference regions to the maxima or minima from the one or more reaction regions. The activity of an enzyme is detected.

In another embodiment, a method is provided for detecting the activity of an enzyme in a self-referencing colorimetric resonant optical biosensor comprising one or more liquid-holding vessels and comprising a colorimetric resonant optical biosensor as a surface of the liquid-holding vessels. One or more specific binding substances are immobilized on a first portion of a colorimetric resonant optical biosensor to form a reaction surface and no specific binding substances are immobilized on a second portion of the colorimetric resonant optical biosensor of each liquid-holding vessel forming a reference surface. The method comprises (i) applying one or more enzymes in a reaction volume to the one or more liquid holding vessels; (ii) illuminating the one or more reaction surfaces and the one or more reference surfaces with light; (iii) detecting a maxima in reflected wavelength, or a minima in transmitted wavelength of light from the one or more reaction surfaces and the one or more reference surfaces; and (iv) comparing the maxima or minima of the one or more reference surfaces to the maxima or minima from the one or more reaction surfaces. The activity of an enzyme is detected.

In another embodiment, a method is provided for detecting the inhibition activity of one or more molecules against one or more enzymes or specific binding partners in a self-referencing colorimetric resonant optical biosensor comprising one or more liquid-holding vessels and comprising a colorimetric resonant optical biosensor as a bottom surface of the liquid holding vessels. A fluid-impermeable divider forms assay regions. One or more specific binding substances are immobilized on one or more of the assay regions to form reaction regions and one or more assay regions do not have immobilized specific binding substances to form reference regions. The method comprises (i) applying one or more molecules suspected of having inhibition activity in a reaction volume to the one or more liquid holding vessels; (ii) applying one or more enzymes or specific binding partners in a reaction volume; (iii) illuminating the one or more reaction regions and the one or more reference regions with light; (iv) detecting a maxima in reflected wavelength, or a minima in transmitted wavelength of light from the one or more reaction regions and the one or more reference regions; and (v) comparing the maxima or minima of the one or more reference regions to the maxima or minima from the one or more reaction regions. Inhibition activity of the one or more molecules is detected.

In another embodiment, a method is provided for detecting the inhibition activity of one or more molecules against one or more enzymes or specific binding partners in a self-referencing colorimetric resonant optical biosensor. The biosensor comprises one or more liquid-holding vessels comprising a colorimetric resonant optical biosensor as a surface. One or more specific binding substances are immobilized on a first portion of a colorimetric resonant optical biosensor to form a reaction surface and no specific binding substances are immobilized on a second portion of the colorimetric resonant optical biosensor of each liquid-holding vessel forming a reference surface. The method comprises (i) applying one or more molecules suspected of having inhibition activity in a reaction volume to the one or more liquid holding vessels; (ii) applying one or more enzymes to the one or more liquid holding vessels; (iii) illuminating the one or more reaction surfaces and the one or more reference surfaces with light; (iv) detecting a maxima in reflected wavelength, or a minima in transmitted wavelength of light from the one or more reaction surfaces and the one or more reference surfaces; and (v) comparing the maxima or minima of the one or more reference surfaces to the maxima or minima from the one or more reaction surfaces. The inhibition activity of the one or more molecules is detected.

The advantages of self-referencing colorimetric resonant optical biosensors of the invention and the use thereof are related to their enhanced ability to account for experimental errors caused by bulk refractive index shifts, nonspecific binding, temperature effects, mixing effects, sensor variability, and others. Because the reference surfaces or regions exist in the same liquid-holding vessel as the reaction surfaces or regions, absolutely identical experimental conditions are applied to the reference and reaction surfaces or regions at the same time, making the reference more accurate than if it were performed in its own, separate liquid-holding vessel. Such accurate detection and subtraction of experimental errors allow otherwise untenable experiments to be conducted, such as, for example, the detection of small molecules with low affinities and low concentrations requiring measurement of peak wavelength shift signals that are near the noise resolution limit of readout instruments. The self-referencing colorimetric resonant optical biosensors of the invention and methods of use thereof also allow more accurate measurement of otherwise experimentally obtainable results, as well as economy of reagents and apparatus due to reaction and reference residing in the same liquid-holding vessel.

BRIEF DESCRIPTION OF THE DRAWINGS

FIG. 1A shows a cross-sectional view of a biosensor wherein light is shown as illuminating the bottom of the biosensor; however, light can illuminate the biosensor from either the top or the bottom. FIG. 1B shows a diagram of a biosensor wherein light is shown as illuminating the bottom of the biosensor; however, light can illuminate the biosensor from either the top or the bottom;

FIG. 6A shows a biosensor that is incorporated into a microtiter plate. FIG. 6B shows a biosensor in a microarray slide format.

FIG. 7A shows an exemplary self-referencing colorimetric resonant optical biosensor comprising the bottom surface of a liquid-holding vessel. A specific binding substance has been immobilized onto the biosensor surface, thereby defining a reaction surface. A biosensor surface in which no specific binding substance is immobilized defines a reference surface. FIG. 7B shows the addition of a specific binding partner. Subtraction of the measured colorimetric resonant optical peak wavelength value (PWV) of the reference surface from the PWV from the reaction surface yields the actual PWV shift due to the addition of the specific binding partner. As the reference and reaction surfaces reside, for example, in the same microtiter plate well, experimental artifacts, such as, for example, bulk refractive index shifts, non-specific binding effects, temperature effects, mixing artifacts and pipetting errors, are more accurately accounted for.

FIG. 9A demonstrates that control of a molecular surface pattern is generated by a biomolecular cleavage event. In the fluorescence image, streptavidin-Cy5 is only detected in the regions where NHS-PEG-Biotin ligand solution was applied, while no streptavidin-Cy5 is detected in the regions where no ligand solution was applied. FIG. 9B is an image of the biosensor peak wavelength value as a function of position within the same well, where light regions indicate more positive peak wavelength value shifts due to streptavidin-Cy5 binding. FIG. 9B shows that imaging according to the methods of the invention, or "BIND" imaging, provides an accurate picture of locations where differential binding has occurred within the same liquid vessel due to the selective application of ligand receptor solution to the biosensor surface.

DETAILED DESCRIPTION OF THE INVENTION

Figure 1A:
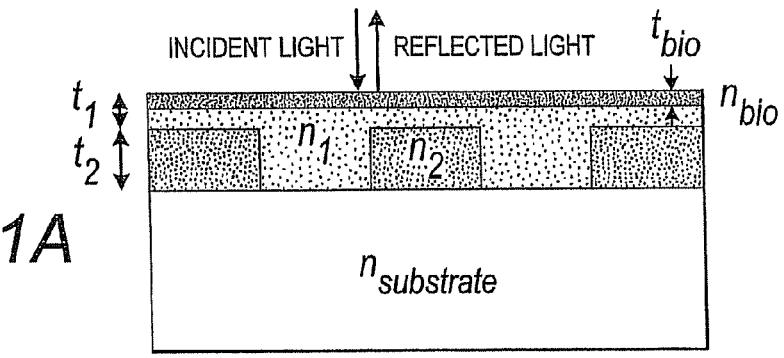
FIG. 1A-B.

A colorimetric resonant optical biosensor allows biochemical interactions to be measured on the biosensor's surface without the use of fluorescent tags, colorimetric labels or any other type of tag or label. See U.S. application Ser. No. 01/050,723 (filed Oct. 23, 2001), U.S. application Ser. No. 01/045,455 (filed Oct. 23, 2001), U.S. application Ser. No. 10/058,626 (filed Jan. 28, 2002), and U.S. application Ser. No. 10/059,060 (filed Jan. 28, 2002), incorporated herein by reference in their entirety. A biosensor surface contains an optical structure that, when illuminated with collimated white light, is designed to reflect only a narrow band of wavelengths. The narrow wavelength band is described as a wavelength "peak." The "peak wavelength value" (PWV) changes when materials, such as biological materials, are deposited or removed from the biosensor surface. A readout instrument is used to illuminate distinct locations on a biosensor surface with collimated white light, and to collect collimated reflected light. The collected light is gathered into a wavelength spectrometer for determination of PWV. In addition, it is possible to replace the single point spectrometer with an imaging spectrometer system that can measure the peak reflected wavelength as a function of position across the biosensor surface.

A biosensor structure can be incorporated into standard disposable laboratory items such as microtiter plates by bonding the structure (biosensor side up) into the bottom of a bottomless microtiter plate cartridge. Incorporation of a biosensor into common laboratory format cartridges is desirable for compatibility with existing microtiter plate handling equipment such as mixers, incubators, and liquid dispensing equipment.

The functional advantages of each of the assay methods defined in this disclosure arise from the properties of a colorimetric resonant optical biosensor. First, biochemical interactions are measured without the use of labels. Second, many interactions can be monitored simultaneously. Third, the biosensor is incorporated into a liquid holding vessel, such as a standard microtiter plate, for isolation and liquid containment of parallel assays.

For the majority of assays currently performed for genomics, proteomics, pharmaceutical compound screening, and clinical diagnostic applications, fluorescent or colorimetric chemical labels are commonly attached to the molecules under study so they may be readily visualized. Because attachment of a label substantially increases assay complexity and possibly alters the functionality of molecules through conformational modification or epitope blocking, various label-free biosensor technologies have emerged. Label-free detection phenomenologies include measuring changes in mass, microwave transmission line characteristics, microcantilever deflection, or optical density upon a surface that is activated with a receptor molecule with high affinity for a detected molecule. The widespread commercial acceptance of label-free biosensor technologies has been limited by their ability to provide high detection sensitivity and high detection parallelism in a format that is inexpensive to manufacture and package. For example, biosensors fabricated upon semiconductor or glass wafers in batch photolithography, etch and deposition processes are costly to produce and package if the biosensor area is to be large enough to contain large numbers of parallel assays. Similarly, the requirement of making electrical connections to individual biosensors in an array poses difficult challenges in terms of package cost and compatibility with exposure of the biosensor to fluids.

Definitions

"Microtiter plate," as used herein, is defined as a microtiter or multiwell plate of 2, 6, 8, 24, 48, 96, 384, 1536 or 3456 well formats, or any other number of wells.

"Test reagent," as used herein, is defined as any specific binding partner, enzyme, or chemical compound and solutions thereof. Non-limiting examples of enzymes are proteases, lipases, nucleases, lyases, peptidases, hydrolases, ligases, kinases and phosphatases. In addition to the enzymes, chemical compounds and solutions thereof, "test reagent" also refers to buffer blanks thereof. A buffer blank refers to reagents or solutions identical in composition to those added to the other recited test reagents, with the enzyme component omitted.

"Inhibition activity" is defined herein as the ability of a molecule or compound to slow or stop another molecule from carrying out catalytic activity. For example, a compound that has inhibition activity of a protease inhibits the protease from cleaving a protein. Such inhibition activity is carried out "against" the catalytic molecule. "Inhibition activity" also means the ability of a molecule or compound to substantially inhibit or partially inhibit the binding of a binding partner to a specific binding substance.

"Combinatorial chemical library" is defined herein as a diverse set of molecules resulting from the combination of their constituent building block materials in a myriad of ways.

Subwavelength Structured Surface (SWS) Biosensor

In one embodiment of the invention, a colorimetric resonant optical biosensor comprises a subwavelength structured surface (SWS), which is used to create a sharp optical resonant reflection at a particular wavelength that can be used to track with high sensitivity the interaction of biological materials, such as specific binding substances or binding partners or both. An SWS acts as a surface binding platform for specific binding substances.

Subwavelength structured surfaces are an unconventional type of diffractive optic that can mimic the effect of thin-film coatings. (Peng & Morris, "Resonant scattering from two-dimensional gratings," J. Opt. Soc. Am. A, Vol. 13, No. 5, p. 993, May 1996; Magnusson, & Wang, "New principle for optical filters," Appl. Phys. Lett., 61, No. 9, p. 1022, August, 1992; Peng & Morris, "Experimental demonstration of resonant anomalies in diffraction from two-dimensional gratings," Optics Letters, Vol. 21, No. 8, p. 549, April, 1996). A SWS structure contains a one-dimensional, two-dimensional, or three dimensional grating in which the grating period is small compared to the wavelength of incident light so that no diffractive orders other than the reflected and transmitted zeroth orders are allowed to propagate. A SWS surface narrowband filter can comprise a grating sandwiched between a substrate layer and a cover layer that fills the grating grooves.

Optionally, a cover layer is not used. When the effective index of refraction of the grating region is greater than the substrate or the cover layer, a waveguide is created. When a filter is designed properly, incident light passes into the waveguide region and propagates as a leaky mode. A grating structure selectively couples light at a narrow band of wavelengths into the waveguide. The light propagates only a very short distance, undergoes scattering, and couples with the forward- and backward-propagating zeroth-order light. This highly sensitive coupling condition can produce a resonant grating effect on the reflected radiation spectrum, resulting in a narrow band of reflected or transmitted wavelengths. The depth and period of the grating are less than the wavelength of the resonant grating effect.

The reflected or transmitted color of this structure can be modulated by the addition of molecules such as specific binding substances or binding partners or both to the upper surface of the cover layer or the grating surface. The added molecules increase the optical path length of incident radiation through the structure, and thus modify the wavelength at which maximum reflectance or transmittance will occur.

In one embodiment, a biosensor, when illuminated with white light, is designed to reflect only a single wavelength or a narrow band of wavelengths. When specific binding substances are attached to the surface of the biosensor, the reflected wavelength is shifted due to the change of the optical path of light that is coupled into the grating. By linking specific binding substances to a biosensor surface, complementary binding partner molecules can be detected without the use of any kind of fluorescent probe, particle label or any other type of label. The detection technique is capable of resolving changes of, for example, ~0.1 nm thickness of protein binding, and can be performed with the biosensor surface either immersed in fluid or dried.

A detection system consists of, for example, a light source that illuminates a small spot of a biosensor at normal incidence through, for example, a fiber optic probe, and a spectrometer that collects the reflected light through, for example, a second fiber optic probe also at normal incidence. Because no physical contact occurs between the excitation/detection system and the biosensor surface, no special coupling prisms are required and the biosensor can be easily adapted to any commonly used assay platform including, for example, microtiter plates and microarray slides. A single spectrometer reading can be performed in several milliseconds, thus it is possible to quickly measure a large number of molecular interactions taking place in parallel upon a biosensor surface, and to monitor reaction kinetics in real time.

While illumination of a small region through an optical fiber probe and detection with a single point spectrometer collects an averaged resonant signal across the illuminated area, it is possible to replace the single point spectrometer with an imaging spectrometer system that can measure the peak reflected wavelength as a function of position across the biosensor surface with pixel resolution of ~15 microns. With such an imaging readout system, the detection of a specific binding substance-binding pattern within, for example, a liquid-holding vessel can be performed that is capable of resolving biosensor regions that are smaller than the 0.5-3.0 mm spot of the single spectrometer system. In this case, multiple specific binding substance regions can be defined on the biosensor surface, where each region holds a different specific binding substance, and multiple non-specific binding substance regions can be defined to serve as reference locations within the vessel.

This technology is useful in applications where large numbers of biomolecular interactions are measured in parallel, particularly when molecular labels would alter or inhibit the functionality of the molecules under study. High-throughput screening of pharmaceutical compound libraries with protein targets, and microarray screening of protein-protein interactions for proteomics are examples of applications that require the sensitivity and throughput afforded by the compositions and methods of the invention.

Figure 1B:
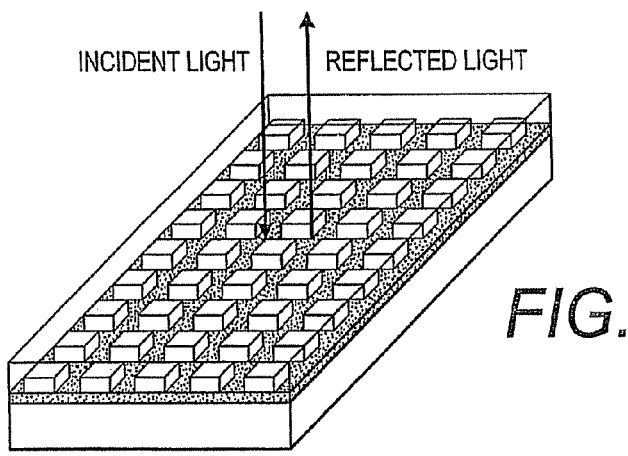

FIGS. 1A and 1B are diagrams of an example of a two-dimensional colorimetric resonant reflection diffractive grating biosensor. In FIG. 1, $n_{substrate}$ represents a substrate material. $n_2$ represents the refractive index of an optical grating. $n_1$ represents an optional cover layer. $n_{bio}$ represents the refractive index of one or more specific binding substances. $t_1$ represents the thickness of the optional cover layer above the one-, two- or three-dimensional grating structure. $t_2$ represents the thickness of the grating. $t_{bio}$ represents the thickness of the layer of one or more specific binding substances. In one embodiment, are $n_2 > n_1$ (see FIG. 1A). Layer thicknesses (i.e. cover layer, one or more specific binding substances, or an optical grating) are selected to achieve resonant wavelength sensitivity to additional molecules on the top surface. The grating period is selected to achieve resonance at a desired wavelength. The resonance grating effect produced from such a colorimetric resonant reflection diffractive grating biosensor is described above.

A biosensor comprises an optical grating comprised of a high refractive index material, a substrate layer that supports the grating, and one or more specific binding substances immobilized on the surface of the grating opposite of the substrate layer. Optionally, a cover layer covers the grating surface. An optical grating is coated with a high refractive index dielectric film which can be comprised of a material that includes, for example, zinc sulfide, titanium dioxide, tantalum oxide, and silicon nitride. A cross-one-, two-, or three-dimensional grating with optical features can comprise any periodically repeating function, for example, a "square-wave." An optical grating can also comprise a repeating pattern of shapes selected from the group consisting of lines, squares, circles, ellipses, triangles, trapezoids, sinusoidal waves, ovals, rectangles, and hexagons. A biosensor of the invention can also comprise an optical grating comprised of, for example, plastic or epoxy, which is coated with a high refractive index material.

Biosensor Characteristics

Figure 2:
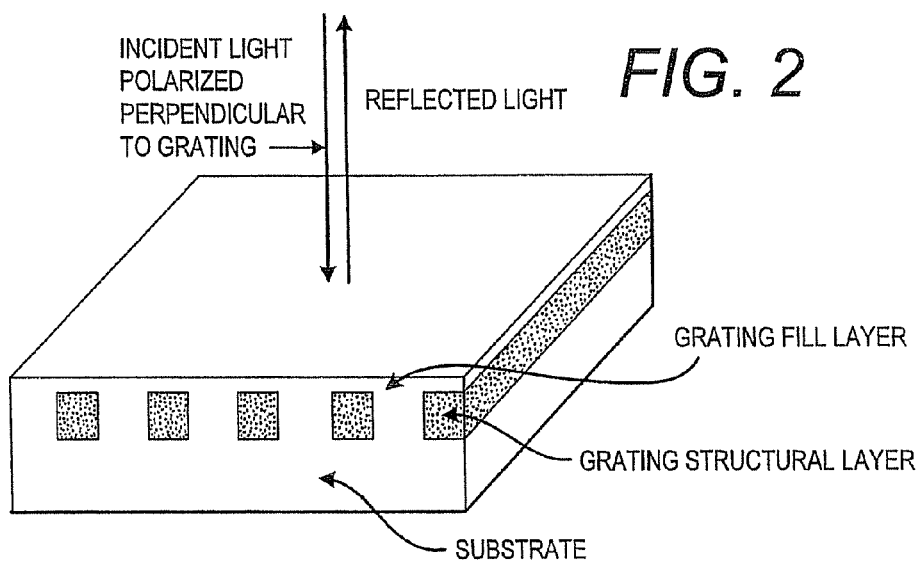
FIG. 2 shows an embodiment of a colorimetric resonant reflection biosensor comprising a one-dimensional grating.

Linear gratings (i.e., one dimensional gratings) have resonant characteristics where the illuminating light polarization is oriented perpendicular to the grating period. A schematic diagram of one embodiment a linear grating structure with an optional cover layer is shown in FIG. 2. A colorimetric resonant reflection biosensor can also comprise, for example, a two-dimensional grating, e.g., a hexagonal array of holes or squares. See, e.g., FIG. 4. Other shapes can be used as well. A linear grating has the same pitch (i.e. distance between regions of high and low refractive index), period, layer thicknesses, and material properties as a hexagonal array grating. However, light must be polarized perpendicular to the grating lines in order to be resonantly coupled into the optical structure. Therefore, a polarizing filter oriented with its polarization axis perpendicular to the linear grating must be inserted between the illumination source and the biosensor surface. Because only a small portion of the illuminating light source is correctly polarized, a longer integration time is required to collect an equivalent amount of resonantly reflected light compared to a hexagonal grating.

An optical grating can also comprise, for example, a "stepped" profile, in which high refractive index regions of a single, fixed height are embedded within a lower refractive index cover layer. The alternating regions of high and low refractive index provide an optical waveguide parallel to the top surface of the biosensor.

It is also possible to make a resonant biosensor in which the high refractive index material is not stepped, but which varies with lateral position. The high refractive index material of a two-dimensional grating can be sinusoidally varying in height. To produce a resonant reflection at a particular wavelength, the period of the sinusoid is identical to the period of an equivalent stepped structure. The resonant operation of the sinusoidally varying structure and its functionality as a biosensor has been verified using GSOLVER (Grating Solver Development Company, Allen, Tex., USA) computer models.

A biosensor of the invention can further comprise a cover layer on the surface of an optical grating opposite of a substrate layer. Where a cover layer is present, the one or more specific binding substances are immobilized on the surface of the cover layer opposite of the grating. Preferably, a cover layer comprises a material that has a lower refractive index than a material that comprises the grating. A cover layer can be comprised of, for example, glass (including spin-on glass (SOG)), epoxy, or plastic.

For example, various polymers that meet the refractive index requirement of a biosensor can be used for a cover layer. SOG can be used due to its favorable refractive index, ease of handling, and readiness of being activated with specific binding substances using the wealth of glass surface activation techniques. When the flatness of the biosensor surface is not an issue for a particular system setup, a grating structure of SiN/glass can directly be used as the sensing surface, the activation of which can be done using the same means as on a glass surface.

Resonant reflection can also be obtained without a planarizing cover layer over an optical grating. For example, a biosensor can contain only a substrate coated with a structured thin film layer of high refractive index material. Without the use of a planarizing cover layer, the surrounding medium (such as air or water) fills the grating. Therefore, specific binding substances are immobilized to the biosensor on all surfaces of an optical grating exposed to the specific binding substances, rather than only on an upper surface.

In general, a biosensor of the invention will be illuminated with white light that will contain light of every polarization angle. The orientation of the polarization angle with respect to repeating features in a biosensor grating will determine the resonance wavelength. For example, a "linear grating" (i.e., a one-dimensional grating) biosensor consisting of a set of repeating lines and spaces will have two optical polarizations that can generate separate resonant reflections. Light that is polarized perpendicularly to the lines is called "s-polarized," while light that is polarized parallel to the lines is called "p-polarized." Both the s and p components of incident light exist simultaneously in an unfiltered illumination beam, and each generates a separate resonant signal. A biosensor can generally be designed to optimize the properties of only one polarization (the s-polarization), and the non-optimized polarization is easily removed by a polarizing filter.

Figure 3:
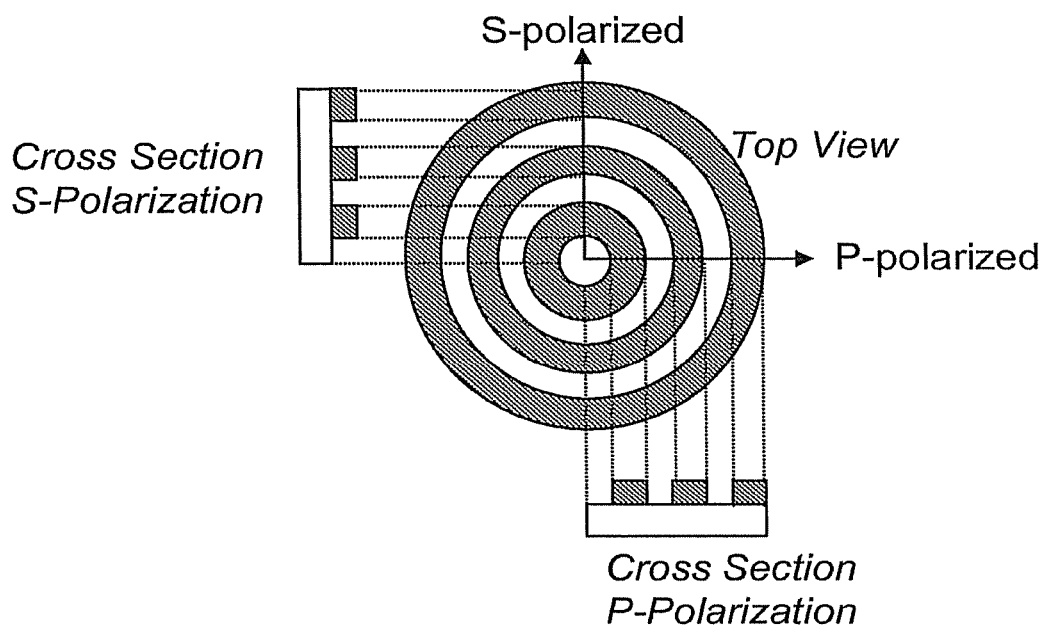
FIG. 3 shows a resonant reflection or transmission filter structure consisting of a set of concentric rings.

In order to remove the polarization dependence, so that every polarization angle generates the same resonant reflection spectra, an alternate biosensor structure can be used that consists of a set of concentric rings. In this structure, the difference between the inside diameter and the outside diameter of each concentric ring is equal to about one-half of a grating period. Each successive ring has an inside diameter that is about one grating period greater than the inside diameter of the previous ring. The concentric ring pattern extends to cover a single biosensor location—an array spot, reaction region or a microtiter plate well. Each separate microarray spot, reaction region or microtiter plate well has a separate concentric ring pattern centered within it. See, e.g., FIG. 3. All polarization directions of such a structure have the same cross-sectional profile. The concentric ring structure must be illuminated precisely on-center to preserve polarization independence. The grating period of a concentric ring structure is less than the wavelength of the resonantly reflected light. The grating period is about 0.01 micron to about 1 micron. The grating depth is about 0.01 to about 1 micron.

Figure 4:
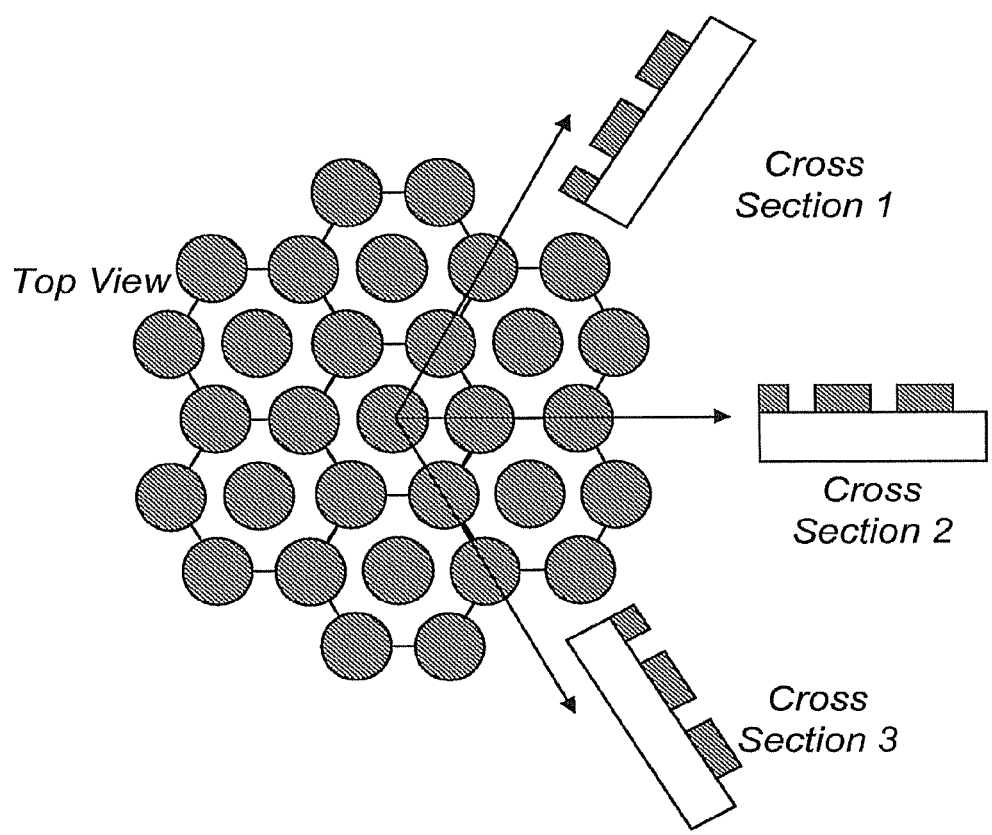
FIG. 4 shows a resonant reflective or transmission filter structure comprising a hexagonal grid of holes (or a hexagonal grid of posts) that closely approximates the concentric circle structure of FIG. 3 without requiring the illumination beam to be centered upon any particular location of the grid.

In another embodiment, an array of holes or posts are arranged to closely approximate the concentric circle structure described above without requiring the illumination beam to be centered upon any particular location of the grid. See e.g. FIG. 4. Such an array pattern is automatically generated by the optical interference of three laser beams incident on a surface from three directions at equal angles. In this pattern, the holes (or posts) are centered upon the corners of an array of closely packed hexagons as shown in FIG. 4. The holes or posts also occur in the center of each hexagon. Such a hexagonal grid of holes or posts has three polarization directions that "see" the same cross-sectional profile. The hexagonal grid structure, therefore, provides equivalent resonant reflection spectra using light of any polarization angle. Thus, no polarizing filter is required to remove unwanted reflected signal components. The period of the holes or posts can be about 0.01 microns to about 1 micron and the depth or height can be about 0.01 microns to about 1 micron.

Another grating that can be produced using the methods of the invention is a volume surface-relief volume diffractive grating (a SRVD grating), also referred to as a three-dimensional grating. SRVD gratings have a surface that reflects predominantly at a particular narrow band of optical wavelengths when illuminated with a broad band of optical wavelengths. Where specific binding substances and/or binding partners are immobilized on a SRVD grating, producing a SRVD biosensor, the reflected narrow band of wavelengths of light is shifted. One-dimensional surfaces, such as thin film interference filters and Bragg reflectors, can select a narrow range of reflected or transmitted wavelengths from a broadband excitation source, however, the deposition of additional material, such as specific binding substances and/or binding partners onto their upper surface results only in a change in the resonance linewidth, rather than the resonance wavelength. In contrast, SRVD biosensors have the ability to alter the reflected wavelength with the addition of material, such as specific binding substances and/or binding partners to the surface. The depth and period of relief volume diffraction structures are less than the resonance wavelength of light reflected from a biosensor.

A three-dimensional surface-relief volume diffractive grating can be, for example, a three-dimensional phase-quantized terraced surface relief pattern whose groove pattern resembles a stepped pyramid. When such a grating is illuminated by a beam of broadband radiation, light will be coherently reflected from the equally spaced terraces at a wavelength given by twice the step spacing times the index of refraction of the surrounding medium. Light of a given wavelength is resonantly diffracted or reflected from the steps that are a half-wavelength apart, and with a bandwidth that is inversely proportional to the number of steps.

An example of a three-dimensional phase-quantized terraced surface relief pattern is a pattern that resembles a stepped pyramid. Each inverted pyramid is approximately 1 micron in diameter, preferably, each inverted pyramid can be about 0.5 to about 5 microns diameter, including for example, about 1 micron. The pyramid structures can be close-packed so that a typical microarray spot with a diameter of about 150-200 microns can incorporate several hundred stepped pyramid structures. One reaction surface or reaction region of specific binding substance can comprise many thousands of stepped pyramid structures. The relief volume diffraction structures have a period of about 0.1 to about 1 micron and a depth of about 0.1 to about 1 micron. Individual microarray locations (with an entire microarray spot or reaction surface or reaction region incorporating hundreds of pyramids now represented by a single pyramid for one microarray spot, reaction surface or reaction region) can be optically queried to determine if specific binding substances or binding partners are adsorbed onto the surface. When the biosensor is illuminated with white light, pyramid structures without significant bound material will reflect wavelengths determined by the step height of the pyramid structure. When higher refractive index materials, such as binding partners or specific binding substances, are incorporated over the reflective metal surface, the reflected wavelength is modified to shift toward longer wavelengths. The color that is reflected from the terraced step structure is theoretically given as twice the step height times the index of refraction of a reflective material that is coated onto the first surface of a sheet material of a SRVD biosensor. A reflective material can be, for example silver, aluminum, or gold.

One or more specific binding substances, as described above, are immobilized on the reflective material of a SRVD biosensor. One or more specific binding substances can be arranged in an ordered or disordered array of one or more distinct locations, as described above, on the reflective material, comprising microarray spots, reaction surfaces or reaction regions.

Because the reflected wavelength of light from a SRVD biosensor is confined to a narrow bandwidth, very small changes in the optical characteristics of the surface manifest themselves in easily observed changes in reflected wavelength spectra. The narrow reflection bandwidth provides a surface adsorption sensitivity advantage compared to reflectance spectrometry on a flat surface.

A SRVD biosensor reflects light predominantly at a first single optical wavelength when illuminated with a broad band of optical wavelengths, and reflects light at a second single optical wavelength when one or more specific binding substances are immobilized on the reflective surface. The reflection at the second optical wavelength results from optical interference. A SRVD biosensor also reflects light at a third single optical wavelength when the one or more specific binding substances are bound to their respective binding partners, due to optical interference.

Readout of the reflected color can be performed serially by focusing a microscope objective onto individual microarray spots, reaction surfaces or reaction regions and reading the reflected spectrum, or in parallel by, for example, projecting the reflected image of the microarray, reaction surface or reaction region onto a high resolution color CCD camera.

Self-Referencing Colorimetric Resonant Optical Biosensors

A non-self-referencing colorimetric resonant optical biosensor comprises a colorimetric resonant optical biosensor that is a surface, such as a bottom surface, of a liquid-holding vessel. The colorimetric resonant optical biosensor can have one or more specific binding substances immobilized on it. The specific binding substances are applied by, for example, filling an entire liquid-holding vessel with a liquid solution containing specific binding substance molecules, and allowing the specific binding substances to immobilize to the biosensor surface. After immobilization, any non-bound specific binding substances are rinsed away so that the only specific binding substances remaining are bound to the biosensor surface. In order to provide an experimental control, a second separate liquid containing vessel is prepared in close physical proximity to the one containing the specific binding substance, but the second vessel is not exposed to the specific binding substance solution. During the course of a binding experiment, a specific binding partner solution, for example, is dispensed into both vessels. The biosensor within the second vessel acts as a negative experimental control because specific binding substances are not present. Therefore, any biosensor signal generated on the second biosensor can be attributed to experimental artifacts such as nonspecific binding or bulk refractive index variation. The key limitation of this method is that the entire biosensor within the vessel is uniformly coated with the specific binding substance so that the reference biosensor must be in physically different vessel. Any variation from one vessel to another will result in incomplete accounting of effects of bulk refractive index, nonspecific binding, and temperature-induced signals.

The detection of small molecules with low affinities and low concentrations require measurement of peak wavelength shift signals that are near the noise resolution limit of readout instruments. Working with solutions containing small molecules dissolved in solvents such as glycerol or DMSO regularly generates bulk refractive index-induced signals that are as large, or larger than the signal generated by the small molecule binding event. While a separate reference biosensor in a different microtiter well location can be used to compensate for the bulk refractive-index-induced signals, this can potentially reduce the number of usable microtiter well locations by one half However, self-referencing colorimetric resonant optical biosensors can be utilized as both a reference surface or region and a reaction surface or region. Both reference and reaction surfaces can reside in a single liquid-holding vessel, for example, one well of a microtiter plate. Such a self-referencing embodiment increases the efficiency of biosensor usage while providing the best possible reference measurement since both reference (i.e., control) and reaction (i.e., test) surfaces or regions are exposed to identical solvent, temperature and other experimental variable parameters.

The invention provides methods and compositions for designating separate locations on a colorimetric resonant optical biosensor surface within a liquid-holding vessel (such as a microtiter plate well). By application of specific binding substances to only portions of the biosensor surface (reaction surfaces or reaction regions), adjacent regions substantially without specific binding substances (reference surfaces or reference regions) can be used to accurately account for experimental error. Both the reaction surfaces and the reference surfaces are subjected to exactly identical bulk refractive index variation, nonspecific binding, temperature environment, and mixing environment. Thus, the method provides an accurate way to remove these and other experimental artifacts.

The invention also provides methods for performing assays with an arbitrary pattern of specific binding substance locations on a single colorimetric resonant optical biosensor within a liquid holding vessel. Multiple specific binding substances can be applied in a defined pattern so that multiple specific binding substances are simultaneously exposed to the same specific binding partner solution. The specific binding substance pattern can be applied in any arbitrary shape so that the defined shape "appears" as the assay progresses. The shape can be measured with a readout instrument, or, if the biosensor is designed to produce a resonant signal in visual-range wavelengths, can produce a pattern that is readable by eye without instrumentation. See, e.g., FIG. 10.

A self-referencing liquid holding vessel contains one or more portions of a biosensor surface substantially free of specific binding substance, i.e., "reference" surfaces, as well as one or more portions of a biosensor surface containing one or more immobilized specific binding substances, i.e., "reaction" surfaces or regions. Ideally, a reference surface is structurally and chemically identical to a reaction surface or region, minus the specific binding substance (ligand). Reference surfaces or regions and reaction surfaces or regions would either be read simultaneously, or near-simultaneously, and the response recorded on reference surfaces or regions would be, for example, subtracted from reaction surfaces or regions.

In order to produce biosensors that contain surfaces or regions including immobilized specific binding substances (i.e., reaction surfaces or reaction regions) and substantially excluding immobilized specific binding substances (i.e., reference surfaces or reference regions) within a single liquid-holding vessel, a specific binding substance-containing liquid solution can be applied to a biosensor in a manner that allows the specific binding substance to attach to only predetermined areas. Methods for performing this function include, for example, incorporation of a physical barrier within or on the biosensor surface and application of small volumes of specific binding substance solutions to the biosensor surface.

Physical Barrier

A short barrier, also known as a "fluid-impermeable divider," can be built into a surface of or applied to a colorimetric resonant optical biosensor to provide separate assay regions within a liquid-holding vessel, wherein the biosensor comprises a surface, such as the bottom surface, of a liquid-holding vessel. When a specific binding substance solution is dispensed into the liquid-holding vessel, it is only allowed to spread to a predetermined section of the liquid-holding vessel bottom due to the fluid-impermeable divider. An assay region comprising immobilized specific binding substances is a "reaction region." A fluid-impermeable divider that separates the left side of the vessel from the right side can be used, or a fluid-impermeable divider that separates the center portion of the vessel from the outer portion can be used. A fluid-impermeable divider separating the biosensor into a plurality of regions can be used. The fluid-impermeable divider is tall enough so that when specific binding substance solution is dispensed into one region (an "immobilization volume"), it is prevented from flowing into an adjacent assay, reaction, or reference region. When a specific binding partner solution is dispensed into the vessel, its volume is such that the solution is allowed to cover all regions of the vessel bottom at once (a "reaction volume"). That is, a reaction volume can "overflow" the fluid-impermeable divider so that a specific binding partner solution can come in contact with all reaction regions and reference regions within a liquid-holding vessel.

Small Volume Dispensing

A physical barrier is not necessary if the volume of specific binding substance-containing solution is small enough that a single droplet does not entirely cover the assay surface or region of a liquid-holding vessel. For example, if a microtiter plate well is used with a diameter of 7 mm, a droplet of specific binding substance-containing solution can be dispensed into the center of the well, which results in a droplet diameter of only 3 mm. In this case, the center 3 mm of the microtiter well will be used as the "test" part of the assay (i.e., a reaction surface), while the surrounding regions without specific binding substance can function as the reference surface. Automated low volume pipetting systems are commercially available that can reproducibly dispense required volumes (approximately 0.1-3.0 microliters) with the required position accuracy. The size of the dispensed spot will be determined by volume, viscosity, and surface hydrophobicity. This method does not require any physical modification to the biosensor or liquid-holding vessel.

The functional advantages of a self-referencing biosensor of the invention are related to the ability to account for experimental errors caused by bulk refractive index shifts, nonspecific binding, temperature effects, mixing effects, and biosensor variability. Because the reference or control is performed, for example, in the same liquid-holding vessel as the specific binding substance binding experiment, absolutely identical experimental conditions are applied to the reference surfaces and reaction surfaces at the same time, making the reference more accurate than if the reference was performed on a separate liquid-holding device.

Patterning of one or more specific binding substances on the biosensor enables the interaction of multiple specific binding substances to be tested within a single microtiter well, or other liquid-holding vessel, at one time, on the same test sample. This allows closer comparison of the specific binding substance to specific binding partner interactions, and increases the parallelism of assays that can be performed.

Patterning of a specific binding substance within a biosensor enables the formation of specific shapes that can be visualized by a readout instrument or by eye. The pattern that develops during the performance of an assay can be used to indicate a positive or negative outcome of a diagnostic test, for example.

For direct, label-free biodetection of small molecules or molecules at exceedingly low concentrations, the detected signal is often so small that it is lost in the noise introduced by the experiment itself. In these cases, to extract a meaningful binding signal it is critical to be able to accurately subtract the signal caused by experimental and instrumental artifacts from the experimental signal. Several common sources of experimental artifacts are as follows:

Bulk Refractive Index Shift

Because a colorimetric resonant optical biosensor measures changes in total optical density on the biosensor surface, the addition of material to the biosensor that results in a change of the refractive index of the liquid media in contact with the biosensor will induce a signal that is indistinguishable from an actual biochemical binding event. When specific binding substance solutions are partly comprised of salts or solvents (such as DMSO, glycerol, ethanol, etc.), the concentration of salts and solvents will have a measurable effect on the bulk refractive index of the test solution.

Nonspecific Binding

A biosensor surface is typically immobilized with one or more specific binding substances that have the ability to specifically recognize and bind a complementary molecule from a specific binding partner solution. "Specific" binding refers to, for example, the binding of the complementary molecule by its intended receptor on the biosensor surface. "Nonspecific" binding refers to, for example, the physical adsorption of material from the specific binding partner solution that is not due to the intended interaction with the specific binding substance molecule. The unintentionally adsorbed material generates a detectable signal that is not distinguishable from actual detected signal. The present invention provides both reaction surfaces or regions and reference surfaces or regions within a liquid-holding vessel such that both reaction and reference surfaces or regions experience the same nonspecific binding, the signal for which can be more accurately measured and subtracted from the signal due to specific binding.

Reaction and reference surfaces or regions comprising different liquid-holding vessels experience different non-specific binding due to vessel-to-vessel variations in temperature, mixing, pipetting and biosensor surface.

Temperature

For colorimetric resonant optical biosensors, a shift in reflected wavelength can be produced by a change in the temperature of the biosensor. Temperature changes can be induced by changes in the temperature of the ambient environment or changes in temperature of the reagent solution.

Mixing

Physical mixing of the specific binding partner solution in contact with the biosensor surface can produce optical disturbances that produce measurable signals that are not related to actual binding event between specific binding substance and specific binding partner.

Pipetting Errors

Small errors in pipetting volumes of reagents onto, for example, different biosensor wells within the same biosensor microtiter plate can result in bulk refractive shift artifacts that are not identical from well-to-well. Normally, the bulk refractive index effect during an assay can be greatly eliminated by performing an equivalent reference assay in a separate liquid-holding device that does not have a ligand receptor immobilized. If a reaction liquid-holding device and the reference liquid-holding device have slightly different bulk refractive index signals due to pipetting errors, the reference will be inaccurate, and an uncorrectable experiment artifact will be generated.

Biosensor Nonuniformity from Well-to-Well

If a reference biosensor without an immobilized specific binding substance is used to correct for common-mode effects (such as bulk refractive index changes or nonspecific binding), the correction can only be accurate if the reference biosensor has exactly the same sensitivity as the reaction biosensor being studied. The extent that the response of two separate biosensors to the same stimulus is not equal will determine the accuracy of the reference method.

The above experimental artifacts, among others, can substantially affect the results obtained in binding, activity and other assays. Such error can even prevent measurement of many kinds of reactions such as, for example, small molecule and low affinity binding interactions. Unlike other technologies, the present invention accurately accounts for experimental errors and thus affords the researcher greater experimental flexibility and power.

Methods of Making Self-Referencing Colorimetric Resonant Optical Biosensors

Figure 8:
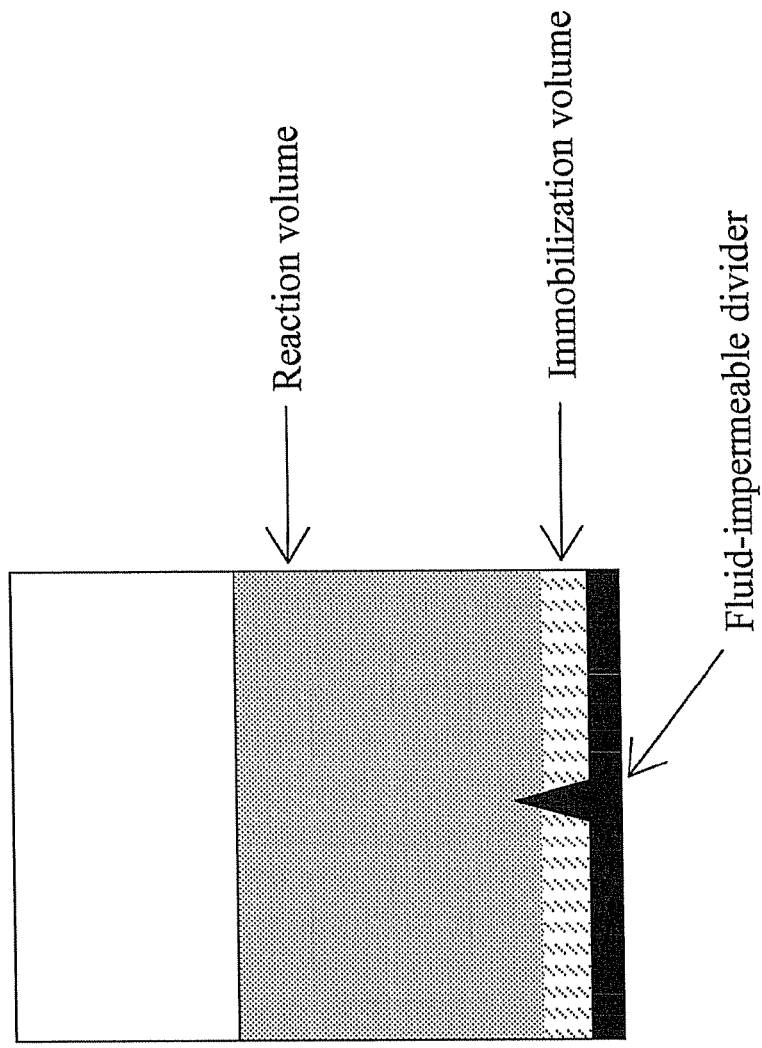
FIG. 8 shows a cross section of one exemplary embodiment of the invention, a self-referencing colorimetric resonant optical biosensor with a fluid-impermeable divider that separates the liquid holding vessel into, for example, two regions. A small volume of specific binding substance, small enough to be retained within one assay region by the fluid-impermeable divider (an immobilization volume), can be added and immobilized to a region thereby defining a reaction region. A biosensor region with no specific binding substance bound can be utilized as a reference region. A volume of reactant, for example, specific binding substance, large enough to encompass all reaction and reference regions (a reaction volume), can be added to the liquid-holding vessel.

Regarding specific binding substance immobilization, the self-referencing colorimetric resonant optical biosensors of the invention comprise biosensors with predefined biosensor surfaces and undefined biosensor surfaces. Predefined surfaces refer to the presence of a "fluid-impermeable barrier" built into or attached to the biosensor surface e.g., FIG. 8. A fluid-impermeable divider segregates the biosensor surface into, generically, "assay regions." Assay regions hold, without overflowing, an "immobilization volume" of sample, for example, specific binding substances. One or more assay regions can have specific binding substances immobilized thereon. When specific binding substances are immobilized on the biosensor surface, in an assay region, it is capable of utilization in an assay and is more precisely referred to as a "reaction region." A biosensor of the invention can have one or more reaction regions. An assay region without specific binding substances immobilized thereon is used as an experimental reference, or control, and is thus referred to as a "reference region." At least two assay regions are needed in a self-referencing colorimetric resonant optical biosensor of the invention, one to be used as a reference region and one as a reaction region.

Figure 7A:
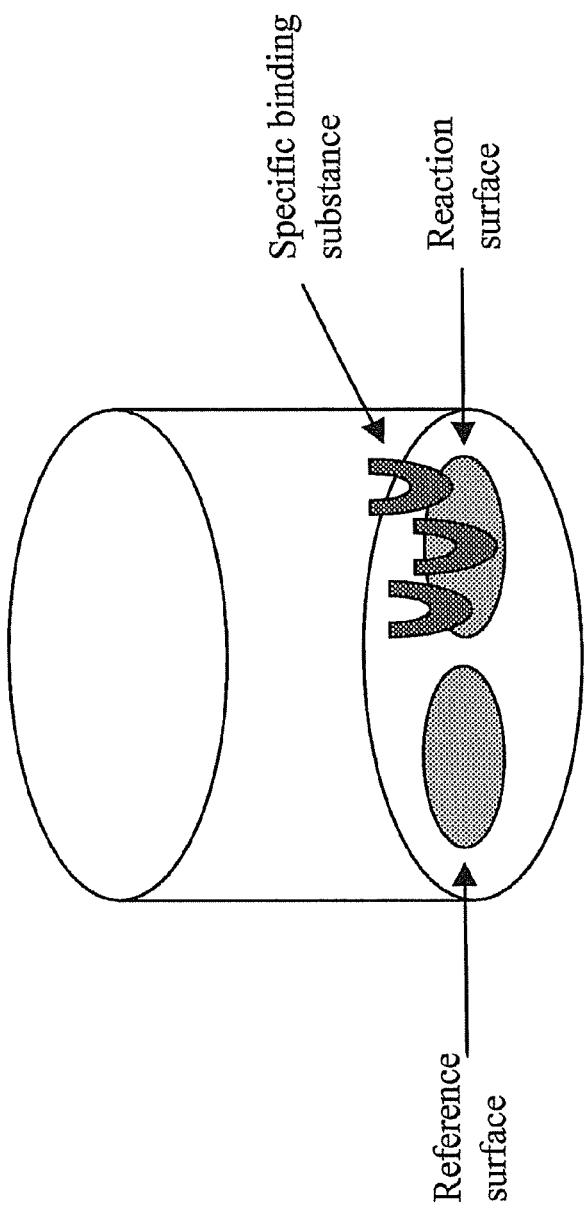
FIGS. 7A-B.

Undefined surfaces refer to the lack of a fluid-impermeable barrier. However, a physical barrier is not necessary if the volume of specific binding substance-containing solution is small enough that it does not entirely cover the biosensor surface. In a self-referencing colorimetric resonant optical biosensor without a fluid-impermeable divider, the entire biosensor surface is an "assay surface." When a small-volume of specific binding substance, an "immobilization volume," is immobilized on a portion of the biosensor surface, it is referred to as a "reaction surface." See FIG. 7A. The absolute volume of an immobilization volume for a biosensor comprising a fluid-impermeable divider or not comprising a fluid-impermeable divider can be the same or different. Generally, immobilization volumes for biosensors comprising a fluid-impermeable divider can be greater. Biosensor surface without specific binding substance immobilized thereon becomes the "reference surface." For example, a single drop of specific binding substance deposited in the middle of biosensor surface (the assay surface) becomes a reaction surface and the surface surrounding the specific binding substance deposition spot can be a reference surface. One or more reaction surfaces and one or more reference surfaces can exist on a biosensor surface.

The self-referencing colorimetric resonant optical biosensors of the invention, comprising either a fluid-impermeable divider or not, can comprise one or more liquid-holding vessels such as, for example, a microtiter plate. One or more colorimetric resonant optical biosensors, with or without fluid-impermeable dividers, comprise one or more surfaces of a liquid-holding vessel. Thus, for example, each well in a 96-well microtiter plate can comprise one or more biosensor surfaces, and each biosensor surface can comprise one or more reaction regions or surfaces and one or more reference regions or surfaces. The liquid-holding vessel can be, for example, selected from the group consisting of a microtiter plate well, a test tube, a Petri dish and a microfluidic channel.

When a self-referencing colorimetric resonant optical biosensor of the invention is illuminated, a resonant grating effect is produced on the reflected radiation spectrum. The depth and period of a grating of a biosensor is less than a wavelength of the resonant grating effect. Further, a narrow band of optical wavelengths can be reflected from the biosensor when the biosensor is illuminated with a broad band of optical wavelengths.

The self-referencing colorimetric resonance optical biosensors of the invention can comprise one or more specific binding substances bound to their specific binding partners. Specific binding partners can be added to any embodiment of self-referencing colorimetric resonance optical biosensor of the invention. For example, if a biosensor comprises a fluid-impermeable divider that segregates the surface into, for example, 16 regions, some of those regions can have immobilization volumes of specific binding substances added thereto (reaction regions) and others can have no specific binding substances added thereto (reference regions). Each immobilization volume preferably does not naturally overflow the fluid-impermeable divider. Continuing the example, specific binding partners can be added in a reaction volume, which is sufficient to overflow the reference and reaction regions, i.e., encompass all assay regions in a liquid-containing vessel. For a self-referencing colorimetric resonance optical biosensor of the invention without a fluid-impermeable divider, a reaction volume of specific binding partner can cover the biosensor surface, encompassing all reaction surfaces and all reference surfaces.

Methods of Using Self-Referencing Colorimetric Resonant Optical Biosensors

Self-referencing colorimetric resonance optical biosensors of the invention can be used, for example, to detect binding of specific binding substances and specific binding partners, the activity of enzymes on specific binding substances and the inhibition activity of molecules on enzyme activity against a specific binding substance or the binding of specific binding partner to specific substance.

Figure 7B:
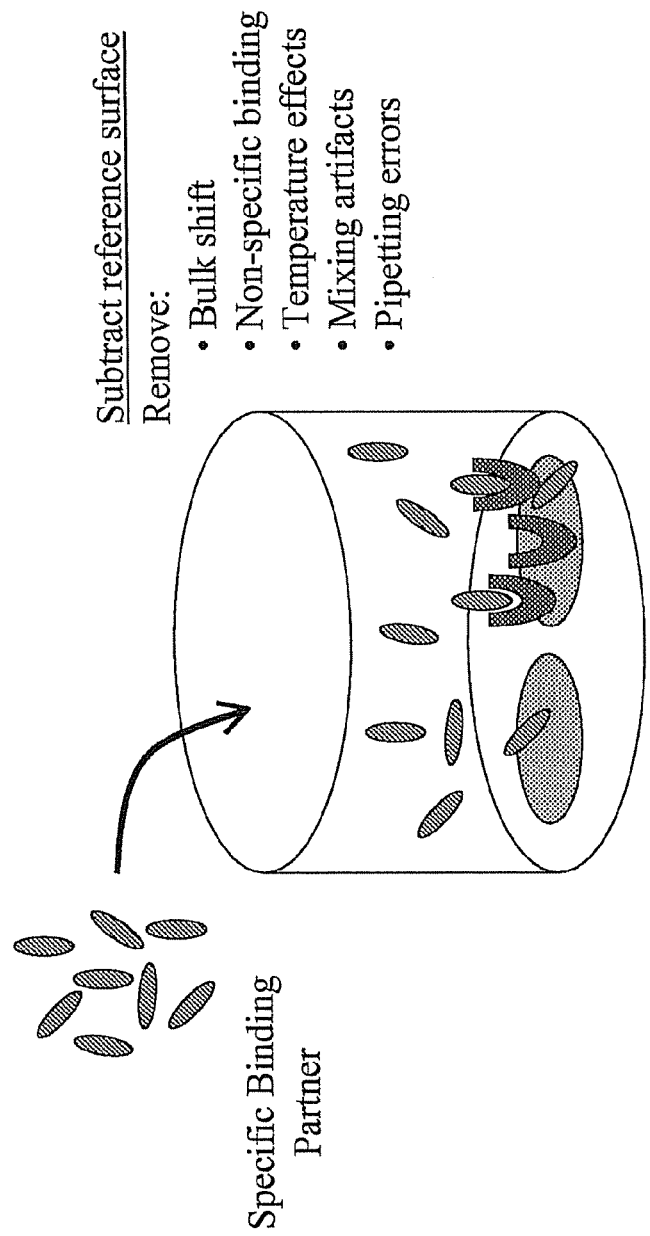

In one example, a method of detecting the binding of one or more specific binding substances to their respective binding partners in a self-referencing colorimetric resonant optical biosensor that comprises one or more liquid-holding vessels can be accomplished by immobilizing an immobilization volume of one or more specific binding substances in one or more reaction regions or surfaces (i.e., in a biosensor with or without a fluid-impermeable divider) and preserving one or more reference regions or surfaces, followed by applying one or more specific binding partners in a reaction volume to the one or more liquid-holding vessels; illuminating the one or more reaction regions or surfaces and the one or more reference regions or surfaces with light; detecting a maxima in reflected wavelength, or a minima in transmitted wavelength of light from the one or more reaction regions or surfaces and the one or more reference regions or surfaces; and comparing the maxima or minima of the one or more reference regions or surfaces to the maxima or minima from the one or more reaction regions or surfaces within a liquid-holding vessel, wherein the binding of one or more specific binding substances to their respective binding partners is detected. See e.g. FIG. 7B.

A method of detecting the activity of an enzyme in a self-referencing colorimetric resonant optical biosensor that comprises one or more liquid-holding vessels can be accomplished by immobilizing an immobilization volume of one or more specific binding substances in one or more reaction regions or surfaces (i.e., in a biosensor with or without a fluid-impermeable divider) and preserving one or more reference regions or surfaces, followed by applying one or more enzymes in a reaction volume to the one or more liquid-holding vessels; illuminating the one or more reaction regions or surfaces and the one or more reference regions or surfaces with light; detecting a maxima in reflected wavelength, or a minima in transmitted wavelength of light from the one or more reaction regions or surfaces and the one or more reference regions or surfaces; and comparing the maxima or minima of the one or more reference regions or surfaces to the maxima or minima from the one or more reaction regions or surfaces within a liquid-holding vessel, wherein the activity of an enzyme is detected.

A method of detecting the inhibition activity of one or more molecules against one or more enzymes or specific binding partners in a self-referencing colorimetric resonant optical biosensor that comprises one or more liquid-holding vessels can be accomplished by immobilizing an immobilization volume of one or more specific binding substance in one or more reaction regions or surfaces (i.e., in a biosensor with or without a fluid-impermeable divider) and preserving one or more reference regions or surfaces, followed by applying one or more molecules suspected of having inhibition activity in a reaction volume to the one or more liquid-holding vessels; applying one or more enzymes or specific binding partners in a reaction volume to the one or more liquid-holding vessels; illuminating the one or more reaction regions or surfaces and the one or more reference regions or surfaces with light;

detecting a maxima in reflected wavelength, or a minima in transmitted wavelength of light from the one or more reaction regions or surfaces and the one or more reference regions or surfaces; and comparing the maxima or minima of the one or more reference regions or surfaces to the maxima or minima from the one or more reaction regions or surfaces within a liquid-holding vessel, wherein the inhibition activity of one or more molecules is detected.

Specific Binding Substances and Binding Partners

One or more specific binding substances are immobilized on the one- or two- or three-dimensional grating or cover layer of a biosensor, if present, by for example, physical adsorption or by chemical binding. A specific binding substance can be, for example, a nucleic acid, peptide, protein solutions, peptide solutions, single or double stranded DNA solutions, RNA solutions, RNA-DNA hybrid solutions, solutions containing compounds from a combinatorial chemical library, antigen, polyclonal antibody, monoclonal antibody, single chain antibody (scFv), F(ab) fragment, $F(ab')_2$ fragment, Fv fragment, small organic molecule, cell, virus, bacteria, polymer or biological sample. A biological sample can be for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, or prostatic fluid. The polymer is selected from the group of long chain molecules with multiple active sites per molecule consisting of hydrogel, dextran, poly-amino acids and derivatives thereof, including poly-lysine (comprising poly-1-lysine and poly-d-lysine), poly-phe-lysine and poly-glu-lysine.

One or more specific binding substances can be arranged in an organized or disorganized array of one or more distinct locations on a biosensor, which define discreet microarray spots, reaction surfaces or reaction regions. An organized or disorganized array of specific binding substances comprises one or more specific binding substances on a surface of a biosensor of the invention such that a surface contains many distinct locations, each with a different specific binding substance or with a different amount of a specific binding substance. For example, an array can comprise 1, 10, 100, 1,000, 10,000 or 100,000 distinct locations. Such a biosensor surface is called an array because one or more specific binding substances are typically laid out in a regular grid pattern in x-y coordinates. However, an array of the invention can comprise one or more specific binding substance laid out in any type of regular or irregular pattern. For example, distinct locations can define an array of spots of one or more specific binding substances. An array spot can be about 50 to about 500 microns in diameter. An array spot can also be about 150 to about 200 microns in diameter. One or more specific binding substances can be bound to their specific binding partners. Alternatively, specific binding substance can be immobilized to define reaction surfaces or reaction regions as described above.

An array on a biosensor of the invention can be created by placing microdroplets of one or more specific binding substances onto, for example, an x-y grid of locations on a grating or cover layer surface. When the biosensor is exposed to a test sample comprising one or more binding partners, the binding partners will be preferentially attracted to distinct locations on the microarray that comprise specific binding substances that have high affinity for the binding partners. Some of the distinct locations will gather binding partners onto their surface, while other locations will not.

A specific binding substance specifically binds to a binding partner that is added to the surface of a biosensor of the invention. A specific binding substance specifically binds to its binding partner, but does not substantially bind other binding partners added to the surface of a biosensor. For example, where the specific binding substance is an antibody and its binding partner is a particular antigen, the antibody specifically binds to the particular antigen, but does not substantially bind other antigens. A binding partner can be, for example, a nucleic acid, peptide, protein solutions, peptide solutions, single or double stranded DNA solutions, RNA solutions, RNA-DNA hybrid solutions, solutions containing compounds from a combinatorial chemical library, antigen, polyclonal antibody, monoclonal antibody, single chain antibody (scFv), F(ab) fragment, $F(ab')_2$ fragment, Fv fragment, small organic molecule, cell, virus, bacteria, polymer or biological sample. A biological sample can be, for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, and prostatic fluid.

One example of an array of the invention is a nucleic acid array, in which each distinct location within the array contains a different nucleic acid molecule. In this embodiment, the spots within the nucleic acid microarray detect complementary chemical binding with an opposing strand of a nucleic acid in a test sample.

While microtiter plates are the most common format used for biochemical assays, microarrays are increasingly seen as a means for maximizing the number of biochemical interactions that can be measured at one time while minimizing the volume of precious reagents. By application of specific binding substances with a microarray spotter onto a biosensor of the invention, specific binding substance densities of 10,000 specific binding substances/$in^2$ can be obtained. By focusing an illumination beam to interrogate a single microarray location, a biosensor can be used as a label-free microarray readout system.

Further, both the microarray and microtiter plate embodiments can be combined such that one or more specific binding substances are arranged in an array of one or more distinct locations on the biosensor surface, said surface residing within one or more wells of the microtiter plate and comprising one or more surfaces of the microtiter plate, preferably the bottom surface. The array of specific binding substances comprises one or more specific binding substances on the biosensor surface within a microtiter plate well such that a surface contains one or more distinct locations, each with a different specific binding substance or with a different amount of a specific binding substance. For example, an array can comprise 1, 10, 100, 1,000, 10,000 or 100,000 distinct locations. Thus, each well of the microtiter plate embodiment can have within it an array of one or more distinct locations separate from the other wells of the microtiter plate embodiment, which allows multiple different samples to be processed on one microtiter plate of the invention, one or more samples for each separate well. The array or arrays within any one well can be the same or different than the array or arrays found in any other microtiter wells of the same microtiter plate.

Immobilization or One or More Specific Binding Substances

Immobilization of one or more binding substances onto a biosensor is performed so that a specific binding substance will not be washed away by rinsing procedures, and so that its binding to binding partners in a test sample is unimpeded by the biosensor surface. Several different types of surface chemistry strategies have been implemented for covalent attachment of specific binding substances to, for example, glass for use in various types of microarrays and biosensors. These same methods can be readily adapted to a biosensor of the invention. Surface preparation of a biosensor so that it contains the correct functional groups for binding one or more specific binding substances is an integral part of the biosensor manufacturing process.

One or more specific binding substances can be attached to a biosensor surface by physical adsorption (i.e., without the use of chemical linkers) or by chemical binding (i.e., with the use of chemical linkers) as well as electrochemical binding, electrostatic binding, hydrophobic binding and hydrophilic binding. Chemical binding can generate stronger attachment of specific binding substances on a biosensor surface and provide defined orientation and conformation of the surface-bound molecules.

Chemical binding of specific binding substances to a biosensor of the invention include, for example, binding via the following functional groups: an amine group, aldehyde group, nickel group, acid group, alkane group, alkene group, alkyne group, aromatic group, alcohol group, ether group, ketone group, ester group, amide group, amino acid group, nitro group, nitrile group, carbohydrate group, thiol group, organic phosphate group, lipid group, phospholipid group or steroid group. These surfaces can be used to attach several different types of chemical linkers to a biosensor surface. For example, an amine surface can be used to attach several types of linker molecules while an aldehyde surface can be used to bind proteins directly, without an additional linker A nickel surface can be used to bind molecules that have an incorporated histidine ("his") tag. Detection of "his-tagged" molecules with a nickel-activated surface is well known in the art (Whitesides, Anal. Chem. 68, 490, (1996)).

Immobilization of specific binding substances to plastic, epoxy, or high refractive index material can be performed essentially as described for immobilization to glass. However, the acid wash step can be eliminated where such a treatment would damage the material to which the specific binding substances are immobilized.

For the detection of binding partners at concentrations less than about ~0.1 ng/ml, it is preferable to amplify and transduce binding partners bound to a biosensor into an additional layer on the biosensor surface. The increased mass deposited on the biosensor can be easily detected as a consequence of increased optical path length. By incorporating greater mass onto a biosensor surface, the optical density of binding partners on the surface is also increased, thus rendering a greater resonant wavelength shift than would occur without the added mass. The addition of mass can be accomplished, for example, enzymatically, through a "sandwich" assay, or by direct application of mass to the biosensor surface in the form of appropriately conjugated beads or polymers of various size and composition. This principle has been exploited for other types of optical biosensors to demonstrate sensitivity increases over 1500× beyond sensitivity limits achieved without mass amplification. See, e.g., Jenison et al., "Interference-based detection of nucleic acid targets on optically coated silicon," Nature Biotechnology, 19: 62-65, 2001.

A NH-2-activated biosensor surface can have a specific binding substance comprising a single-strand DNA capture probe immobilized on the surface. The capture probe interacts selectively with its complementary target binding partner. The binding partner, in turn, can be designed to include a sequence or tag that will bind a "detector" molecule. A detector molecule can contain, for example, a linker to horseradish peroxidase (HRP) that, when exposed to the correct enzyme, will selectively deposit additional material on the biosensor only where the detector molecule is present. Such a procedure can add, for example, 300 angstroms of detectable biomaterial to the biosensor within a few minutes.

A "sandwich" approach can also be used to enhance detection sensitivity. In this approach, a large molecular weight molecule can be used to amplify the presence of a low molecular weight molecule. For example, a binding partner with a molecular weight of, for example, about 0.1 kDa to about 20 kDa, can be tagged with, for example, succinimidyl-6-[a-methyl-a-(2-pyridyl-dithio)toluamido]hexanoate (SMPT), or dimethylpimelimidate (DMP), histidine, or a biotin molecule. Where the tag is biotin, the biotin molecule will binds strongly with streptavidin, which has a molecular weight of 60 kDa. Because the biotin/streptavidin interaction is highly specific, the streptavidin amplifies the signal that would be produced only by the small binding partner by a factor of 60.

Detection sensitivity can be further enhanced through the use of chemically derivatized small particles. "Nanoparticles" made of colloidal gold, various plastics, or glass with diameters of about 3-300 nm can be coated with molecular species that will enable them to covalently bind selectively to a binding partner. For example, nanoparticles that are covalently coated with streptavidin can be used to enhance the visibility of biotin-tagged binding partners on the biosensor surface. While a streptavidin molecule itself has a molecular weight of 60 kDa, the derivatized bead can have a molecular weight of any size, including, for example, 60 KDa. Binding of a large bead will result in a large change in the optical density upon the biosensor surface, and an easily measurable signal. This method can result in an approximately 1000× enhancement in sensitivity resolution.

Liquid-Holding Vessels

Figure 6B:
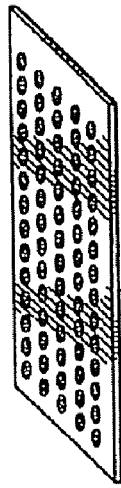
FIGS. 6A-B shows two biosensor formats that can incorporate a colorimetric resonant optical biosensor.
Figure 6A:
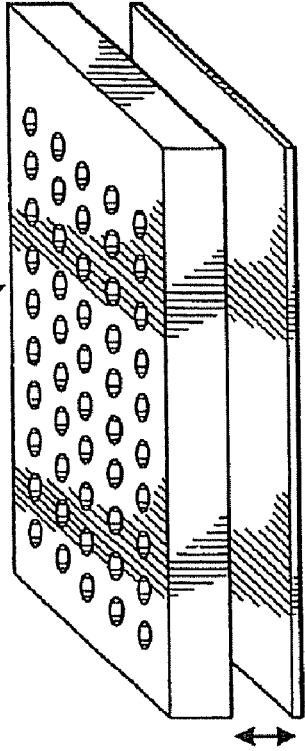

A self-referencing colorimetric resonant optical biosensor of the invention can comprise an inner surface, for example, a bottom surface of a liquid-holding vessel. A liquid-holding vessel can be, for example, a microtiter plate well, a test tube, a petri dish, or a microfluidic channel. One embodiment of the invention is a biosensor that is incorporated into any type of microtiter plate. For example, a biosensor can be incorporated into the bottom surface of a microtiter plate by assembling the walls of the reaction vessels over the resonant reflection surface, as shown in FIGS. 6A and 6B, so that each reaction "spot" can be exposed to a distinct test sample. Therefore, each individual microtiter plate well can act as a separate reaction vessel. Separate chemical reactions can, therefore, occur within adjacent wells without intermixing reaction fluids and chemically distinct test solutions can be applied to individual wells.

Several methods for attaching a biosensor or grating of the invention to the bottom surface of bottomless microtiter plates can be used, including, for example, adhesive attachment, ultrasonic welding, and laser welding.

The most common assay formats for pharmaceutical high-throughput screening laboratories, molecular biology research laboratories, and diagnostic assay laboratories are microtiter plates. The plates are standard-sized plastic cartridges that can contain about 2, 6, 8, 24, 48, 96, 384, 1536 or 3456 individual reaction vessels arranged in a grid. Due to the standard mechanical configuration of these plates, liquid dispensing, robotic plate handling, and detection systems are designed to work with this common format. A biosensor of the invention can be incorporated into the bottom surface of a standard microtiter plate. See, e.g., FIG. 6A. Because the biosensor surface can be fabricated in large areas, and because the readout system does not make physical contact with the biosensor surface, an arbitrary number of individual biosensor areas can be defined that are only limited by the focus resolution of the illumination optics and the x-y stage that scans the illumination/detection probe across the biosensor surface.

Methods of Using Biosensors

Biosensors of the invention can be used to study one or a number of specific binding substance/binding partner interactions in parallel. Binding of one or more specific binding substances to their respective binding partners can be detected, without the use of labels, by applying one or more binding partners to a biosensor that have one or more specific binding substances immobilized on their surfaces. A biosensor is illuminated with light and a maxima in reflected wavelength, or a minima in transmitted wavelength of light is detected from the biosensor. If one or more specific binding substances have bound to their respective binding partners, then the reflected wavelength of light is shifted as compared to a situation where one or more specific binding substances have not bound to their respective binding partners. Where a biosensor is coated with an array of one or more distinct locations containing the one or more specific binding substances, then a maxima in reflected wavelength or minima in transmitted wavelength of light is detected from each distinct location of the biosensor.

Figure 5:
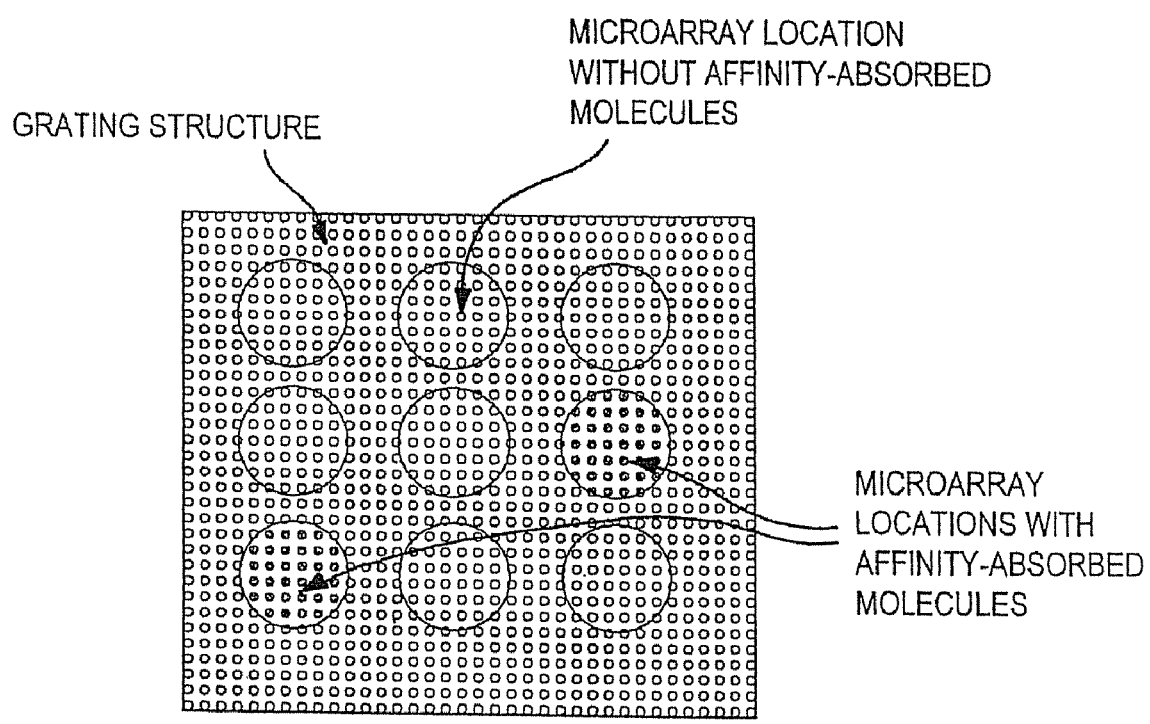
FIG. 5 shows an example of a biosensor used as a microarray.

In one embodiment of the invention, a variety of specific binding substances, for example, antibodies, can be immobilized in an array format onto a biosensor of the invention. See, e.g., FIG. 5. The biosensor is then contacted with a test sample of interest comprising binding partners, such as proteins. Only the proteins that specifically bind to the antibodies immobilized on the biosensor remain bound to the biosensor. Such an approach is essentially a large-scale version of an enzyme-linked immunosorbent assay; however, the use of an enzyme or fluorescent label is not required. For high-throughput applications, biosensors can be arranged in an array of arrays, wherein several biosensors comprising an array of specific binding substances are arranged in an array. In another embodiment, a biosensor can occur on the tip of a fiber probe for in vivo detection of biochemical substance.

The activity of an enzyme can be detected by applying one or more enzymes to a biosensor to which one or more specific binding substances have been immobilized. The biosensor is washed and illuminated with light. The reflected wavelength of light is detected from the biosensor. Where the one or more enzymes have altered the one or more specific binding substances of the biosensor by enzymatic activity by, for example, cleaving all or a portion of a specific binding substance from the surface of a biosensor the reflected wavelength of light is shifted.

Another embodiment of the invention is a method of detecting cleavage of one or more entire specific binding substances from a surface of a colorimetric resonant optical biosensor. The method involves immobilizing one or more binding substances onto the surface of the colorimetric resonant optical biosensor at a distinct location, detecting a PWV of the distinct location, applying one or more cleaving molecules, detecting a PWV of the distinct location and comparing the initial PWV with the subsequent PWV. The cleavage of one or more entire specific binding substances is detected, and a peak wavelength value (PWV) is a relative measure of the specific binding substance that is bound to the biosensor. A cleaving molecule is a molecule that can cleave another molecule. For example, a cleaving molecule can be an enzyme such as a proteases, lipases, nucleases, lyases, peptidases, hydrolases, ligases, kinases and phosphatases.

A colorimetric resonant optical biosensor can comprise an internal surface of a microtiter well, a microtiter plate, a test tube, a petri dish or a microfluidic channel. Immobilization of the specific binding substance can be affected via binding to, for example, the following functional groups: a nickel group, an amine group, an aldehyde group, an acid group, an alkane group, an alkene group, an alkyne group, an aromatic group, an alcohol group, an ether group, a ketone group, an ester group, an amide group, an amino acid group, a nitro group, a nitrile group, a carbohydrate group, a thiol group, an organic phosphate group, a lipid group, a phospholipid group or a steroid group. Further, the specific binding substance is immobilized on the surface of the colorimetric resonant optical biosensor via physical adsorption, chemical binding, electrochemical binding, electrostatic binding, hydrophobic binding or hydrophilic binding.

One or more specific binding substances can be arranged in an array of one or more distinct locations on the surface of the biosensor. The one or more distinct locations can define microarray spots of about 50-500 microns, or about 150-200 microns in diameter.

The method described above, that of detecting cleavage of one or more entire specific binding substances from a surface of a colorimetric resonant optical biosensor, can also comprise alternative steps. One or more specific binding substances can be immobilized in one or more distinct locations defining an array within a well of a microtiter plate. The one or more distinct locations defining the microarray can be located upon the surface of a colorimetric resonant optical biosensor, which, in turn, comprises an internal surface of a well. A PWV is detected for one or more distinct locations within the well. One or more cleaving molecules are applied to the well. Detection of a PWV for one or more distinct locations within the well is performed. The initial PWV and the subsequent PWV are compared. The cleavage of one or more entire specific binding substances at the one or more distinct locations within the well is detected. A peak wavelength value (PWV) is a relative measure of the specific binding substance that is bound to the biosensor.

Another embodiment of the invention provides a method of detecting how effectively a molecule inhibits the activity of an enzyme or binding partner, i.e., "inhibition activity" of the molecule. In one embodiment, is adding one or more molecules suspected of having inhibition activity are added to a biosensor to which one or more specific binding substances are attached, followed by the addition of one or more enzymes known to act upon the specific binding substances. For example, a protease, lipase, nuclease, lyase, peptidase, hydrolase, ligase, kinase, phosphatase, or any other type of enzyme that would produce a detectable change in a specific binding substance. The enzyme can affect a specific binding partner by, for example, cleaving substantially the entire single binding substance or a portion of the single binding substance from the biosensor. One or more binding partners known to bind to one or more specific binding substances immobilized on the biosensor can also be added to the biosensor.

A molecule with no inhibition activity allows the enzyme activity to occur unabated; a molecule with substantially complete inhibition activity halts the reaction substantially completely; and a molecule with partial inhibition halts the reaction partially. Additionally, a molecule with no inhibition activity allows a binding partner to bind to its specific binding substance. A molecule with partial inhibition allows partial or weak binding of the binding partner to its specific binding substance partner. A molecule with inhibition activity inhibits the binding of the binding partner to its specific binding partner. Thus, the method provides a technique of detecting inhibition activity of one or more molecules against enzymes or binding partners.

Detecting a PWV of one or more distinct locations is followed by applying one or more molecules suspected of having inhibition activity to the one or more distinct locations and applying one or more enzymes or binding partners to the distinct locations. The PWV of the one or more distinct locations is detected and compared to the initial PWV. Alternatively, the one or more molecules suspected of having inhibition activity can be mixed with the one or more enzymes or binding partners, which, together, can be applied to the one or more distinct locations. A decrease or increase in the initial PWV above in relation to the subsequent PWV above is (1) a relative measure of the proportion of binding substance that is altered by the enzyme or the amount of binding partners bound to the biosensor from the biosensor surface or (2) a measure of relative effectiveness of one or more molecules suspected of having inhibition activity.

The method described above, that of detecting inhibition activity of one or more molecules against enzymes or binding partners can also comprise alternative steps. For example, one or more specific binding substances can be immobilized in one or more distinct locations defining an array within a well of a microtiter plate or other liquid holding device. The one or more distinct locations defining an array are located upon the surface of a colorimetric resonant optical biosensor which comprises an internal surface of the well. Detecting a PWV for the one or more distinct locations within the well is followed by applying one or more molecules suspected of having inhibition activity to the well. One or more enzymes or binding partners are applied to the well and a PWV is detected for the one or more distinct locations within the well. The initial PWV is compared with the subsequent PWV and reveals the inhibition activity of one or more molecules against enzymes or binding partners at each distinct location within a well. Alternatively, the one or more molecules suspected of having inhibition activity can be mixed with the one or more enzymes or binding partners, which, together, can be applied to the well.

Additionally, a test sample, for example, cell lysates containing binding partners, can be applied to a biosensor of the invention, followed by washing to remove unbound material. The binding partners that bind to a biosensor can be eluted from the biosensor and identified by, for example, mass spectrometry. Optionally, a phage DNA display library can be applied to a biosensor of the invention followed by washing to remove unbound material. Individual phage particles bound to the biosensor can be isolated and the inserts in these phage particles can then be sequenced to determine the identity of the binding partner.

The ability to detect the binding of binding partners to specific binding substances, optionally followed by the ability to detect the removal of substantially entire or partial bound specific binding substances, from one or more distinct locations of the biosensor is an important aspect of the invention. Biosensors of the invention are also capable of detecting and quantifying the amount of a binding partner from a sample that is bound to one or more distinct locations defining an array by measuring the shift in reflected wavelength of light. For example, the wavelength shift at one or more distinct locations can be compared to positive and negative controls at other distinct locations to determine the amount of a specific binding substance that is bound. Importantly, numerous such one or more distinct locations can be arranged on the biosensor surface, and the biosensor can comprise an internal surface of a vessel such as an about 2, 6, 8, 24, 48, 96, 384, 1536 or 3456 well-microtiter plate. As an example, where 96 biosensors are attached to a holding fixture and each biosensor comprises about 100 distinct locations, about 9600 biochemical assays can be performed simultaneously.

Therefore, unlike methods for assays for surface plasmon resonance, resonant mirrors, and waveguide biosensors, the described methods enable many thousands of individual binding reactions to take place simultaneously upon the resonant optical biosensor surface. Clearly, this technology is useful in applications where large numbers of biomolecular interactions are measured in parallel, particularly when molecular labels will alter or inhibit the functionality of the molecules under study. High-throughput screening of pharmaceutical compound libraries with protein targets, and microarray screening of protein-protein interactions for proteomics are examples of applications that require the sensitivity and throughput afforded by this approach.

Self-referencing biosensor techniques can be combined with arrayed specific binding substances techniques such that reaction regions comprise irregular or regular arrays of one or more kinds of specific binding substances, and such reaction surfaces or reaction regions reside within the same liquid-holding vessel as one or more unliganded reference regions.

Detection Systems

A detection system can comprise a biosensor a light source that directs light to the biosensor, and a detector that detects light reflected from the biosensor. In one embodiment, it is possible to simplify the readout instrumentation by the application of a filter so that only positive results over a determined threshold trigger a detection.

A light source can illuminate a biosensor from its top surface, i.e., the surface to which one or more specific binding substances are immobilized or from its bottom surface. By measuring the shift in resonant wavelength at each distinct location of a biosensor of the invention, it is possible to determine which distinct locations have binding partners bound to them. The extent of the shift can be used to determine the amount of binding partners in a test sample and the chemical affinity between one or more specific binding substances and the binding partners of the test sample.

A biosensor can be illuminated twice. The first measurement determines the reflectance spectra of one or more distinct locations of a biosensor array with one or more specific binding substances immobilized on the biosensor. The second measurement determines the reflectance spectra after one or more binding partners are applied to a biosensor. The difference in peak wavelength between these two measurements is a measurement of the amount of binding partners that have specifically bound to a biosensor or one or more distinct locations of a biosensor. This method of illumination can control for small nonuniformities in a surface of a biosensor that can result in regions with slight variations in the peak resonant wavelength. This method can also control for varying concentrations or molecular weights of specific binding substances immobilized on a biosensor.

Single Point Spectrometer Readout

The colorimetric resonant optical biosensor functions by illuminating the surface with collimated white light at normal incidence, and measuring the reflected intensity as a function of wavelength of the reflected light. Typically, a white light source is coupled into an optical fiber that is positioned at normal incidence to the biosensor surface. The output of the fiber casts a small spot of light at the biosensor surface. The diameter of the illuminated spot could be 0.5-2.0 mm, with a 1 mm diameter spot being most typical. The reflected light is gathered by a second optical fiber that is immediately adjacent to the illuminating fiber. The second fiber is connected to the input of a spectrometer.

If there are two distinct regions (ligand versus nonligand) within one liquid vessel that can be separately illuminated and measured, then the measurement of the nonligand regions serves as a reference for the measurement of the ligand region.

Imaging Readout

While illumination of a small region through an optical fiber probe and detection with a single point spectrometer collects an averaged resonant signal across the illuminated area, it is possible to replace the single point spectrometer with an imaging spectrometer system that can measure the peak reflected wavelength as a function of position across the biosensor surface with pixel resolution of ~15 microns. With such an imaging readout system, the detection of a ligand binding pattern within a liquid vessel can be performed that is capable of resolving biosensor regions that are smaller than the 0.5-3.0 mm spot of the single spectrometer system. In this case, multiple ligand regions can be defined on the biosensor surface, where each region holds a different ligand, and multiple non-ligand regions can be defined to serve as reference locations within the vessel.

Computer simulation can be used to determine the expected dependence between a peak resonance wavelength and an angle of incident illumination. A biosensor as shown in, for example, FIG. 1 can be for purposes of demonstration. The substrate chosen was glass ($n_{substrate}$=1.50). The grating is an optical pattern of silicon nitride squares ($t_2$=180 nm, $n_2$=2.01 (n=refractive index), $k_2$=0.001 (k=absorption coefficient)) with a period of 510 nm, and a filling factor of 56.2% (i.e., 56.2% of the surface is covered with silicon nitride squares while the rest is the area between the squares). The areas between silicon nitride squares are filled with a lower refractive index material. The same material also covers the squares and provides a uniformly flat upper surface. For this simulation, a glass layer was selected ($n_1$=1.40) that covers the silicon nitride squares by $t_2$=100 nm.

The reflected intensity as a function of wavelength was modeled using GSOLVER software, which utilizes full 3-dimensional vector code using hybrid Rigorous Coupled Wave Analysis and Modal analysis. GSOLVER calculates diffracted fields and diffraction efficiencies from plane wave illumination of arbitrarily complex grating structures. The illumination can be from any incidence and any polarization.

The simulation shows that there is a strong correlation between the angle of incident light, and the peak wavelength that is measured. This result implies that the collimation of the illuminating beam, and the alignment between the illuminating beam and the reflected beam will directly affect the resonant peak linewidth that is measured. If the collimation of the illuminating beam is poor, a range illuminating angles will be incident on the biosensor surface, and a wider resonant peak will be measured than if purely collimated light were incident.

Because the lower sensitivity limit of a biosensor is related to the ability to determine the peak maxima, it is important to measure a narrow resonant peak. Therefore, the use of a collimating illumination system with the biosensor provides for the highest possible sensitivity.

One type of detection system for illuminating the biosensor surface and for collecting the reflected light is a probe containing, for example, six illuminating optical fibers that are connected to a light source, and a single collecting optical fiber connected to a spectrometer. The number of fibers is not critical, any number of illuminating or collecting fibers are possible. The fibers are arranged in a bundle so that the collecting fiber is in the center of the bundle, and is surrounded by the six illuminating fibers. The tip of the fiber bundle is connected to a collimating lens that focuses the illumination onto the surface of the biosensor.

In this probe arrangement, the illuminating and collecting fibers are side-by-side. Therefore, when the collimating lens is correctly adjusted to focus light onto the biosensor surface, one observes six clearly defined circular regions of illumination, and a central dark region. Because the biosensor does not scatter light, but rather reflects a collimated beam, no light is incident upon the collecting fiber, and no resonant signal is observed. Only by defocusing the collimating lens until the six illumination regions overlap into the central region is any light reflected into the collecting fiber. Because only defocused, slightly uncollimated light can produce a signal, the biosensor is not illuminated with a single angle of incidence, but with a range of incident angles. The range of incident angles results in a mixture of resonant wavelengths due to the strong correlation between the angles of incident light. Thus, wider resonant peaks are measured than might otherwise be possible.

Therefore, it is desirable for the illuminating and collecting fiber probes to spatially share the same optical path. Several methods can be used to co-locate the illuminating and collecting optical paths. For example, a single illuminating fiber, which is connected at its first end to a light source that directs light at the biosensor, and a single collecting fiber, which is connected at its first end to a detector that detects light reflected from the biosensor, can each be connected at their second ends to a third fiber probe that can act as both an illuminator and a collector. The third fiber probe is oriented at a normal angle of incidence to the biosensor and supports counter-propagating illuminating and reflecting optical signals.

Another method of detection involves the use of a beam splitter that enables a single illuminating fiber, which is connected to a light source, to be oriented at a 90 degree angle to a collecting fiber, which is connected to a detector. Light is directed through the illuminating fiber probe into the beam splitter, which directs light at the biosensor. The reflected light is directed back into the beam splitter, which directs light into the collecting fiber probe. A beam splitter allows the illuminating light and the reflected light to share a common optical path between the beam splitter and the biosensor, so perfectly collimated light can be used without defocusing.

Angular Scanning

Detection systems of the invention are based on collimated white light illumination of a biosensor surface and optical spectroscopy measurement of the resonance peak of the reflected beam. Molecular binding on the surface of a biosensor is indicated by a shift in the peak wavelength value, while an increase in the wavelength corresponds to an increase in molecular absorption.

The resonance peak wavelength is strongly dependent on the incident angle of the detection light beam. Because of the angular dependence of the resonance peak wavelength, the incident white light needs to be well collimated. Angular dispersion of the light beam broadens the resonance peak, and reduces biosensor detection sensitivity. In addition, the signal quality from the spectroscopic measurement depends on the power of the light source and the sensitivity of the detector. In order to obtain a high signal-to-noise ratio, an excessively long integration time for each detection location can be required, thus lengthening overall time to readout a biosensor plate. A tunable laser source can be used for detection of grating resonance, but is expensive.

In one embodiment of the invention, these disadvantages are addressed by using a laser beam for illumination of a biosensor, and a light detector for measurement of reflected beam power. A scanning mirror device can be used for varying the incident angle of the laser beam, and an optical system is used for maintaining collimation of the incident laser beam. See, e.g., "Optical Scanning" (Gerald F. Marchall ed., Marcel Dekker (1991). Any type of laser scanning can be used. For example, a scanning device that can generate scan lines at a rate of about 2 lines to about 1,000 lines per second is useful in the invention. In one embodiment of the invention, a scanning device scans from about 50 lines to about 300 lines per second.

In one embodiment, the reflected light beam passes through part of the laser scanning optical system, and is measured by a single light detector. The laser source can be a diode laser with a wavelength of, for example, 780 nm, 785 nm, 810 nm, or 830 nm. Laser diodes such as these are readily available at power levels up to 150 mW, and their wavelengths correspond to high sensitivity of Si photodiodes. The detector thus can be based on photodiode biosensors. A light source provides light to a scanner device, which directs the light into an optical system. The optical system directs light to a biosensor. Light is reflected from the biosensor to the optical system, which then directs the light into a light signal detector. In one embodiment of a detection system, the scanning mirror changes its angular position, the incident angle of the laser beam on the surface changes by nominally twice the mirror angular displacement. The scanning mirror device can be a linear galvanometer, operating at a frequency of about 2 Hz up to about 120 Hz, and mechanical scan angle of about 10 degrees to about 20 degrees. In this example, a single scan can be completed within about 10 msec. A resonant galvanometer or a polygon scanner can also be used. A simple optical system for angular scanning can consists of a pair of lenses with a common focal point between them. The optical system can be designed to achieve optimized performance for laser collimation and collection of reflected light beam.

The angular resolution depends on the galvanometer specification, and reflected light sampling frequency. Assuming galvanometer resolution of 30 arcsec mechanical, corresponding resolution for biosensor angular scan is 60 arcsec, i.e. 0.017 degree. In addition, assume a sampling rate of 100 ksamples/sec, and 20 degrees scan within 10 msec. As a result, the quantization step is 20 degrees for 1000 samples, i.e. 0.02 degree per sample. In this example, a resonance peak width of 0.2 degree, as shown by Peng and Morris (Experimental demonstration of resonant anomalies in diffraction from two-dimensional gratings, Optics Lett., 21:549 (1996)), will be covered by 10 data points, each of which corresponds to resolution of the detection system.

The advantages of such a detection system includes: excellent collimation of incident light by a laser beam, high signal-to-noise ratio due to high beam power of a laser diode, low cost due to a single element light detector instead of a spectrometer, and high resolution of resonance peak due to angular scanning.

Methods for Reading a Self-Referenced Biosensor Well: Single Point Spectrometer Readout A colorimetric resonant optical biosensor functions by illuminating the surface with collimated white light at normal incidence, and measuring the reflected intensity as a function of wavelength of the reflected light. Typically, a white light source is coupled into an optical fiber that is positioned at normal incidence to the biosensor surface. The output of the fiber casts a small spot of light at the biosensor surface. The diameter of the illuminated spot could be 0.5-2.0 mm, with a 1 mm diameter spot being most typical. The reflected light is gathered by a second optical fiber that is immediately adjacent to the illuminating fiber. The second fiber is connected to the input of a spectrometer.

If there are two distinct regions (specific binding substance-containing versus nonspecific binding substance-containing) within one liquid vessel that can be separately illuminated and measured, then the measurement of the reference regions serves as a reference for the measurement of the reaction regions.

Imaging Readout

While illumination of a small region through an optical fiber probe and detection with a single point spectrometer collects an averaged resonant signal across the illuminated area, it is possible to replace the single point spectrometer with an imaging spectrometer system that can measure the peak reflected wavelength as a function of position across the biosensor surface with pixel resolution of ~15 microns. With such an imaging readout system, the detection of a binding pattern within a liquid vessel can be performed that is capable of resolving biosensor regions that are smaller than the 0.5-3.0 mm spot of the single spectrometer system. In this case, multiple specific binding substance regions can be defined on the biosensor surface, where each region holds a different specific binding substance, and multiple non-specific binding substance regions can be defined to serve as reference locations within the vessel.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1

Control of Molecular Surface Pattern

This example demonstrates control of a molecular surface pattern that is generated by a biomolecular cleavage event. Selected regions of a colorimetric resonant optical biosensor embedded within the bottom of a 7 mm diameter microtiter well were treated with a NHS-PEG-biotin solution (Shearwater), the specific binding substance, by applying stripes of specific binding substance with a micropipette tip. The specific binding substance solution was allowed to incubate on the biosensor surface for about 20 minutes before thorough rinsing with water. Following rinsing, the microtiter well was filled with a 1 mg/ml solution of NHS-PEG (Shearwater), which was allowed to incubate in the well for an about 20 minutes. NHS-PEG blocks nonspecific binding of proteins to the biosensor surface. After an additional thorough rinsing with water, a 1 mg/ml solution of streptavidin-Cy5 (Molecular Probes), the specific binding partner, was introduced to the well and allowed to incubate for about 30 minutes. The streptavidin has a strong specific binding interaction with the immobilized biotin on the biosensor surface in the striped pattern. The Cy5 linked to the streptavidin molecule is a fluorescent dye that will allow the combined molecule to be detected by fluorescence confocal microscopy. After a final rinse of the biosensor with water, the pattern of streptavidin-Cy5 binding as a function of spatial location within the microtiter well was imaged with a conventional confocal fluorescence scanner (Affymetrix), and an SRU Biosystems BIND imaging system.

In this system, a white light lamp illuminates the sensor at normal incidence by reflection from a beam-splitting cube. The reflected light is directed through a narrow slit aperture at the input of the imaging spectrometer. Using this method, resonantly reflected light is collected from a single ~15 micron width line on the sensor surface. The imaging spectrometer contains a 2-dimensional CCD camera and a diffraction grating. The "line" of reflected light—containing the biosensor resonance signal—is diffracted to the grating to produce a spatially segregated wavelength spectra from each point within the line. With a CCD camera containing 512×1024 imaging elements, the illuminating line is spatially segregated into 512 points. A spectra, with a resolution of 1024 wavelength data points, is measured for each of the 512 points along the orthogonal axis of the CCD camera. Using this method, the PWVs of 512 points are determined for a single line across the biosensor surface. A motorized stage scans the sensor generating a series of lines which are assembled into an image by software.

Figure 9A:
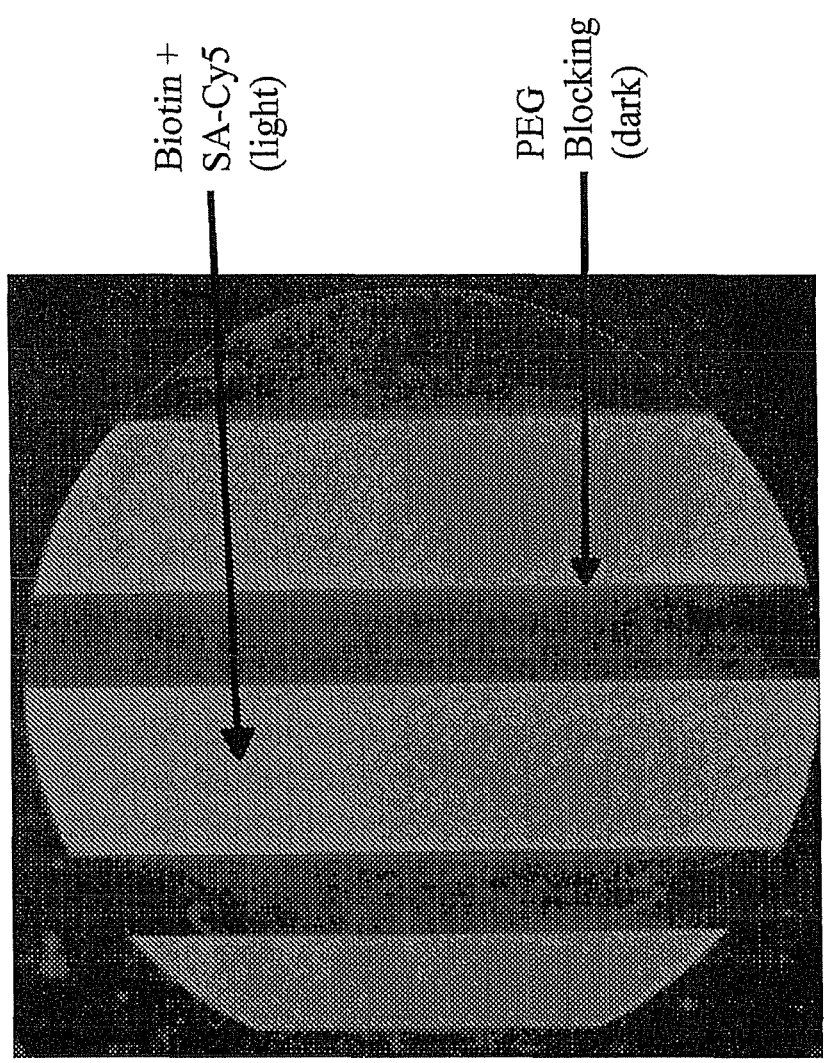
FIGS. 9A-B.
Figure 9B:
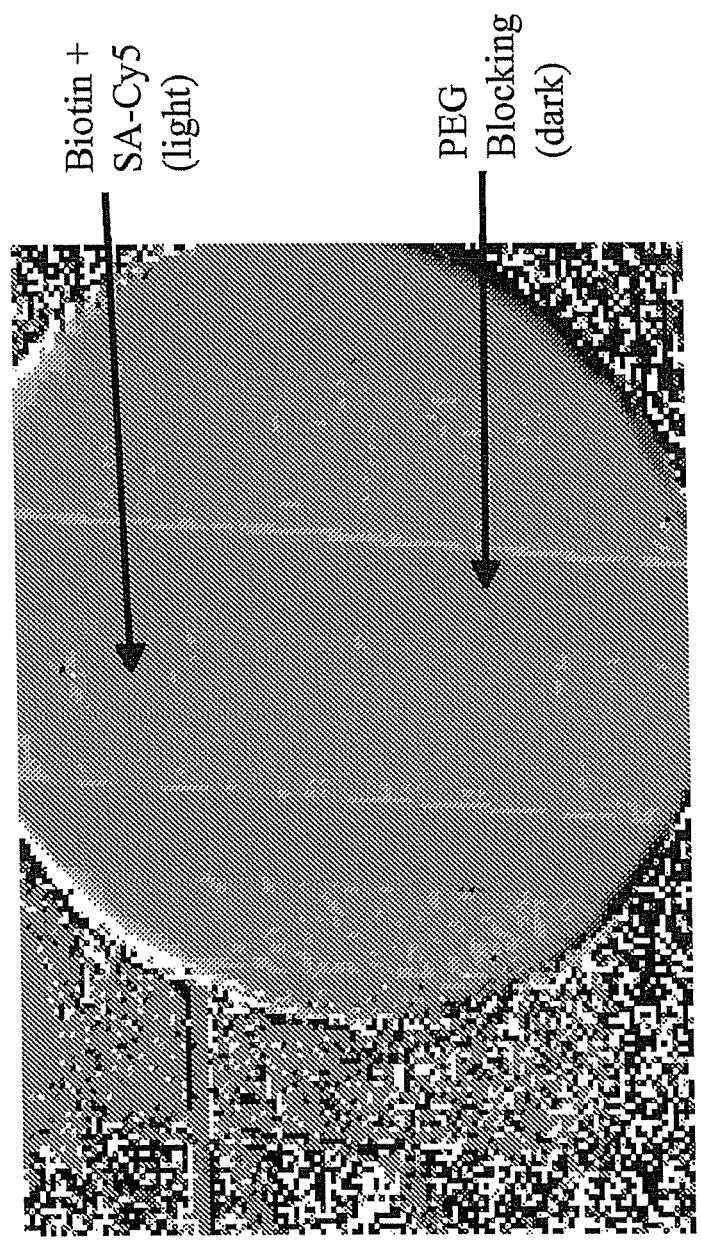

FIG. 9A shows that, in the fluorescence image, streptavidin-Cy5 is only detected in the regions where NHS-PEG-Biotin ligand solution was applied, while no streptavidin-Cy5 is detected in the regions where no ligand solution was applied. FIG. 9B is an image of the biosensor peak wavelength value as a function of position within the same well, where light regions indicate more positive peak wavelength value shifts due to streptavidin-Cy5 binding. FIG. 9B shows that the BIND image provides an accurate picture of locations where differential binding has occurred within the same liquid-holding vessel due to the selective application of ligand receptor solution to the biosensor surface.

Example 2

Arbitrary Biosensor Surface Patterning

Figure 10:
FIG. 10 demonstrates that arbitrary binding patterns can be generated through the application of a ligand to the colorimetric resonant optical biosensor surface in a desired pattern. In this example, gelatin was applied in an "SRU" pattern, followed by exposing the entire biosensor surface to rabbit IgG so that peak wavelength value of the biosensor would be roughly equivalent in all locations. Exposure of the biosensor to collagenase, which selectively cleaves gelatin, effectively removes the gelatin from the surface. As a result, the peak wavelength value in the gelatin reaction surfaces is reduced relative to the reference surfaces without gelatin, which is detected by a BIND imaging system (SRU Biosystems).

This example demonstrates the ability to generate an arbitrary binding pattern through the application of a specific binding substance to the colorimetric resonant optical biosensor surface. A pattern of gelatin (1 mg/ml, Sigma) was applied to a biosensor with a micropipette tip in the shape of the letters "SRU." The gelatin was allowed to incubate on the biosensor surface for about 60 minutes before a thorough rinse with water. Next, the entire biosensor surface was exposed to a 1 mg/ml solution of rabbit IgG (Sigma) that attached a uniform thin layer of protein across the biosensor so that the peak wavelength value of the biosensor would be roughly equivalent in all locations. After a second rinse in water, the entire biosensor was exposed to a 1.5 mg/ml solution of collagenase, a specific binding partner, for about 80 minutes. The collagenase is an enzyme that selectively cleaves gelatin, thus selectively removing protein from the surface only in regions where the gelatin was applied. As the gelatin is cleaved by the collagenase (and the IgG is not) over a 20 minute time period, the peak wavelength value in the gelatin regions is reduced relative to the regions without gelatin. As a consequence of this selective interaction, an image is measured where the word "SRU" appears as a region with lower peak wavelength value compared to surrounding regions, as shown in FIG. 10.

Example 3

Experiment Setup

Plate—96-well biosensor microplate with a central line of UV curable adhesive drawn in the wells by an automated liquid dispensing instrument.

Instrument Setup—Instrument was set up to read 2 spots per well. Each spot was offset from the well center by ±2 mm.

DMSO Concentration Series—A DMSO concentration series of 5% DMSO, 1% DMSO, 0.5% DMSO, and 0.1% DMSO in PBS was added to individual wells of a 96-well biosensor microplate.

Figure 11:
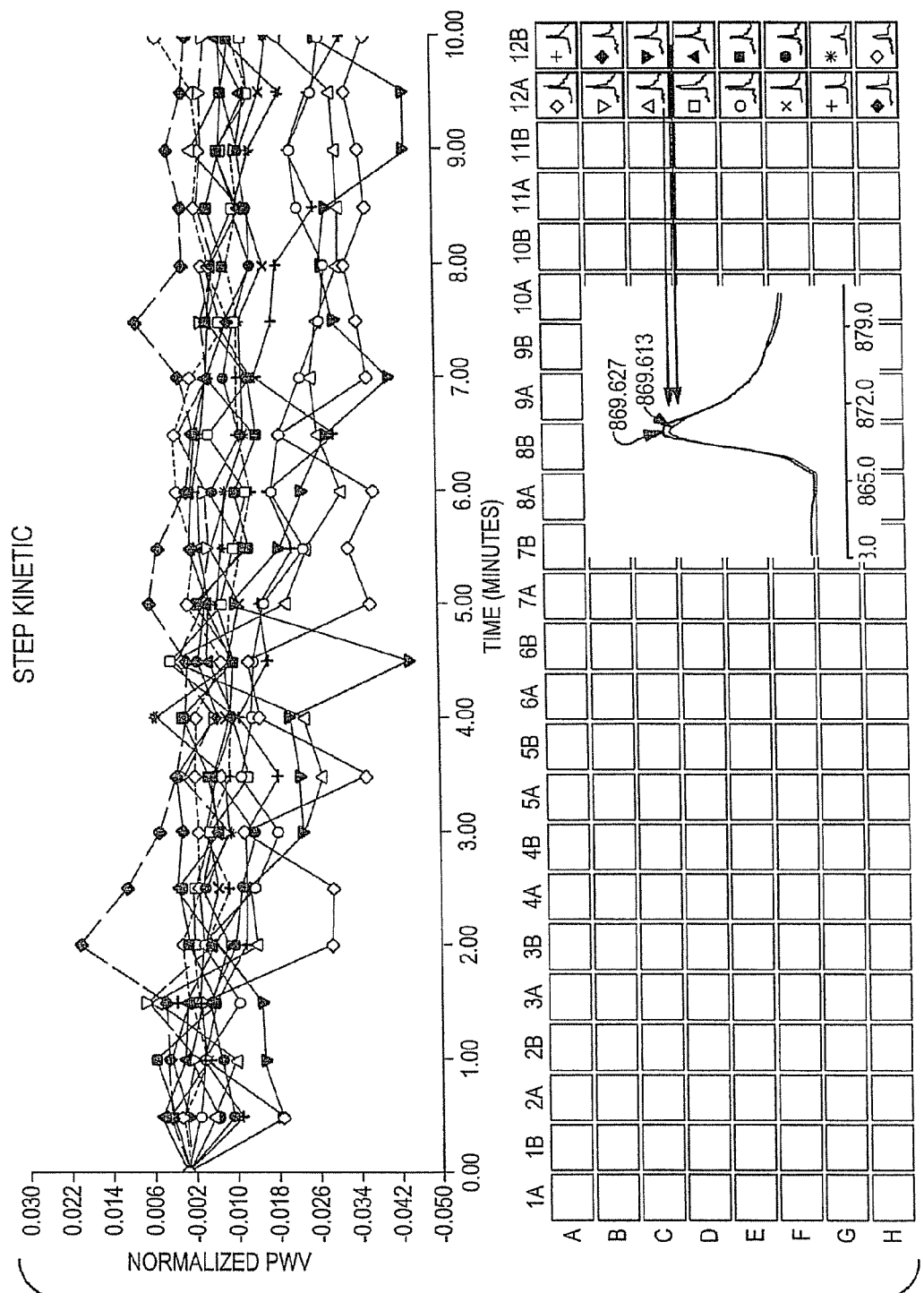
FIG. 11 shows a split-well baseline reading. 90 μL of PBS was added to the wells of column 12. Data was collected over time in 'self-referencing mode.' Inset shows representative overlaid spectra for the left and right sides of a well.

Initial reading. An initial measurement was made to observe the baseline peak wavelength shift over time in the neat wells. Each well contained 90 µL PBS and was read on each side of the barrier. Results are shown in FIG. 11. Baseline drift measurements and peak shape/height read on either side of the well are equivalent.

Figure 12:
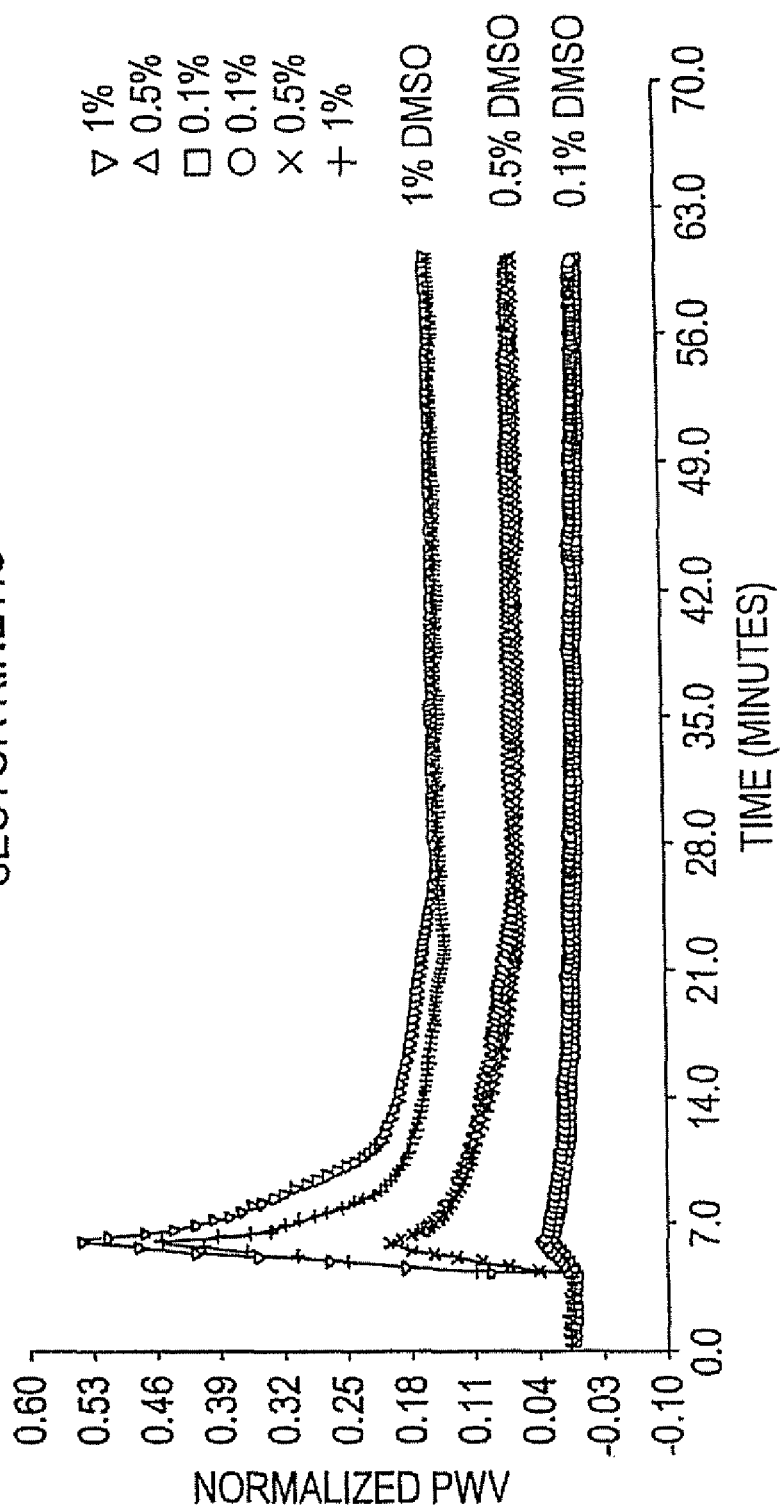
FIG. 12 shows a split-well DMSO reading. The peak wavelength change is plotted over time for DMSO added to different wells at the indicated concentrations. Readings from each side of the wells are plotted and essentially overlay when viewed on this scale. For clarity, the 5% DMSO concentration is not plotted in this figure.
Figure 13:
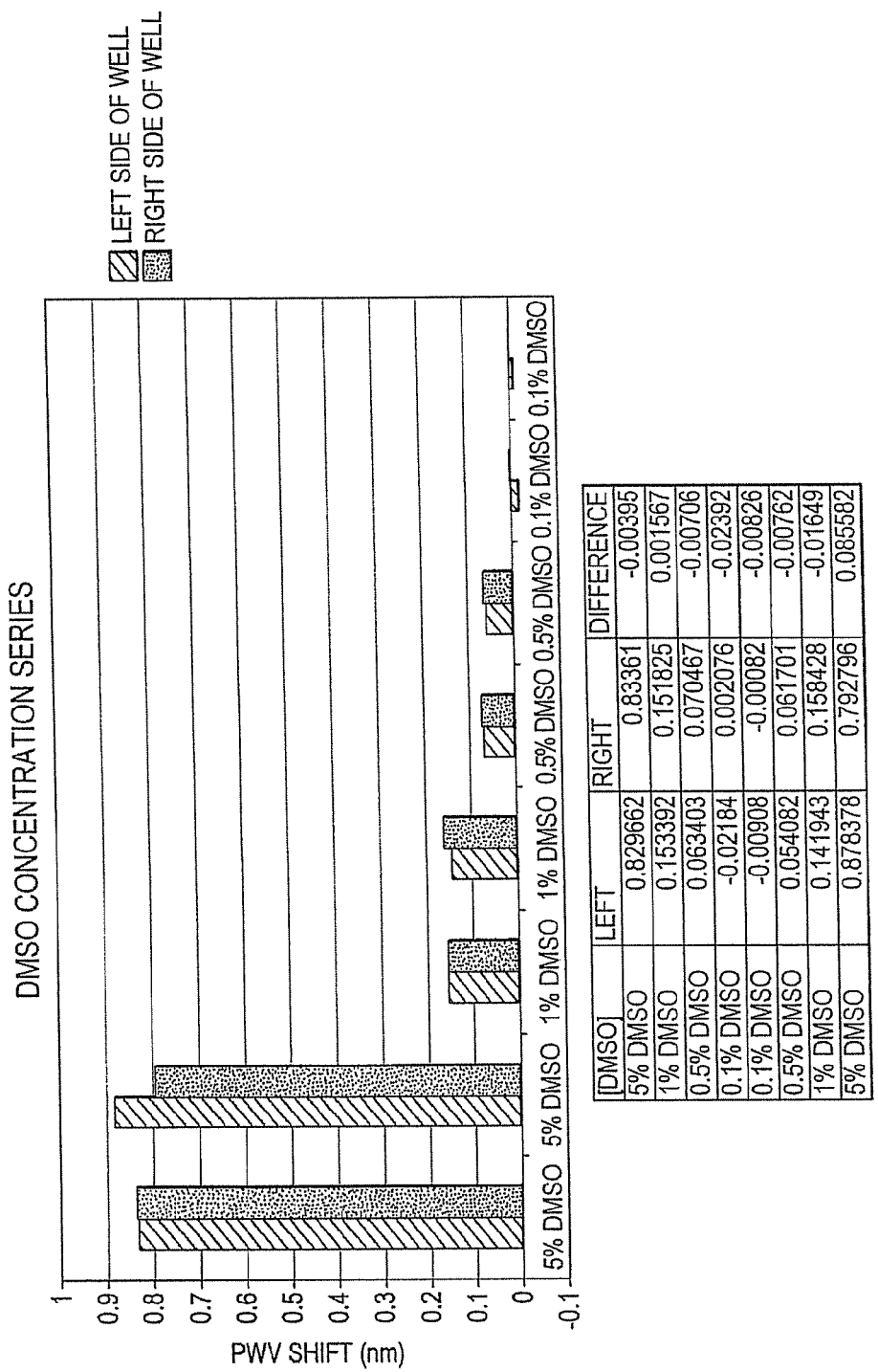
FIG. 13 shows a split well DMSO reading. Endpoint peak wavelength shift values for responses to DMSO bulk shift are plotted. Concentrations are shown in pairs from left to right: 5, 1, 0.5, 0.1%. Shifts for each concentration are shown in the table below the figure. Delta refers to the difference in shift between the left and right side of the well for a given concentration of DMSO.

DMSO reading. DMSO was added to the wells to create a bulk shift response (as a result of DMSO's higher refractive index) in order to compare responses obtained on the right and left sides of each well and demonstrate how a bulk shift artifacts could accurately be corrected for using a self-referencing well. An initial baseline measurement was made to observe the stability of the biosensor plate. Each well contained 90 µL of PBS and was read on each side of the barrier. 10 µL of DMSO was added to each well and allowed to equilibrate. The concentration series was as follows. Row A,H—5% DMSO, Row B,G—1% DMSO, Row C,F—0.1% DMSO, and Row D,E—0.1% DMSO. Results for DMSO shift are shown in FIGS. 12 and 13.

Example 4

Experiment Setup

Plate—96-well biosensor microplate with line of UV curable adhesive drawn by hand down the centers of the wells.

Instrument Setup—Instrument was set up to read 2 spots per well. Each spot was offset from the well center by +1 mm.

ProteinA-IgG Binding—A ProteinA-IgG binding experiment was performed. Protein A was adsorbed to half a well by adding 20 μL of a 0.2 mg/mL solution of Protein A in PBS; 20 μL water was added to the other half of the well. Protein A adsorption was monitored by the readout instrument. Solutions were removed from wells and 100 μL 1 mg/mL gelatin solution was added to block the surfaces. Two different IgG samples were tested for binding to the adsorbed IgG-goat (low affinity) and human (high affinity). IgG's were applied to the wells at 0.1 mg/mL.

Figure 14:
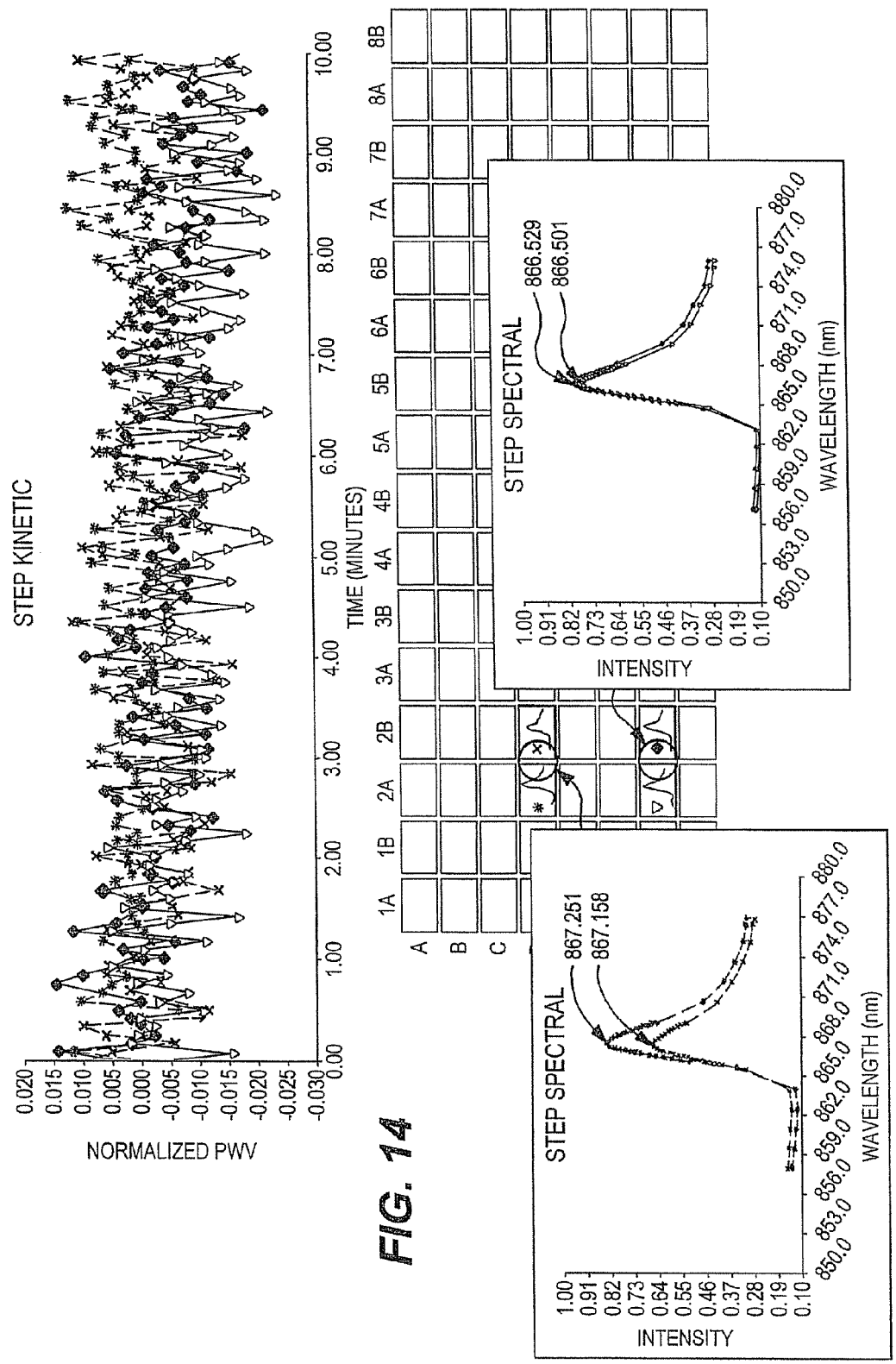
FIG. 14 shows a split-well baseline reading. Two wells containing 100 μL water were read in 'self-referencing mode.' Readings from the left and rights sides of the well essentially overlay. Insets show representative overlaid spectra for the left and right sides of each well.

Initial reading. An initial measurement was made to observe the baseline peak wavelength shift over time in the neat wells. Each well contained 100 μL water and was read on each side of the barrier. Results are shown in FIG. 14. Baseline drift measurements and peak shape/height read on either side of the well are equivalent.

Figure 15:
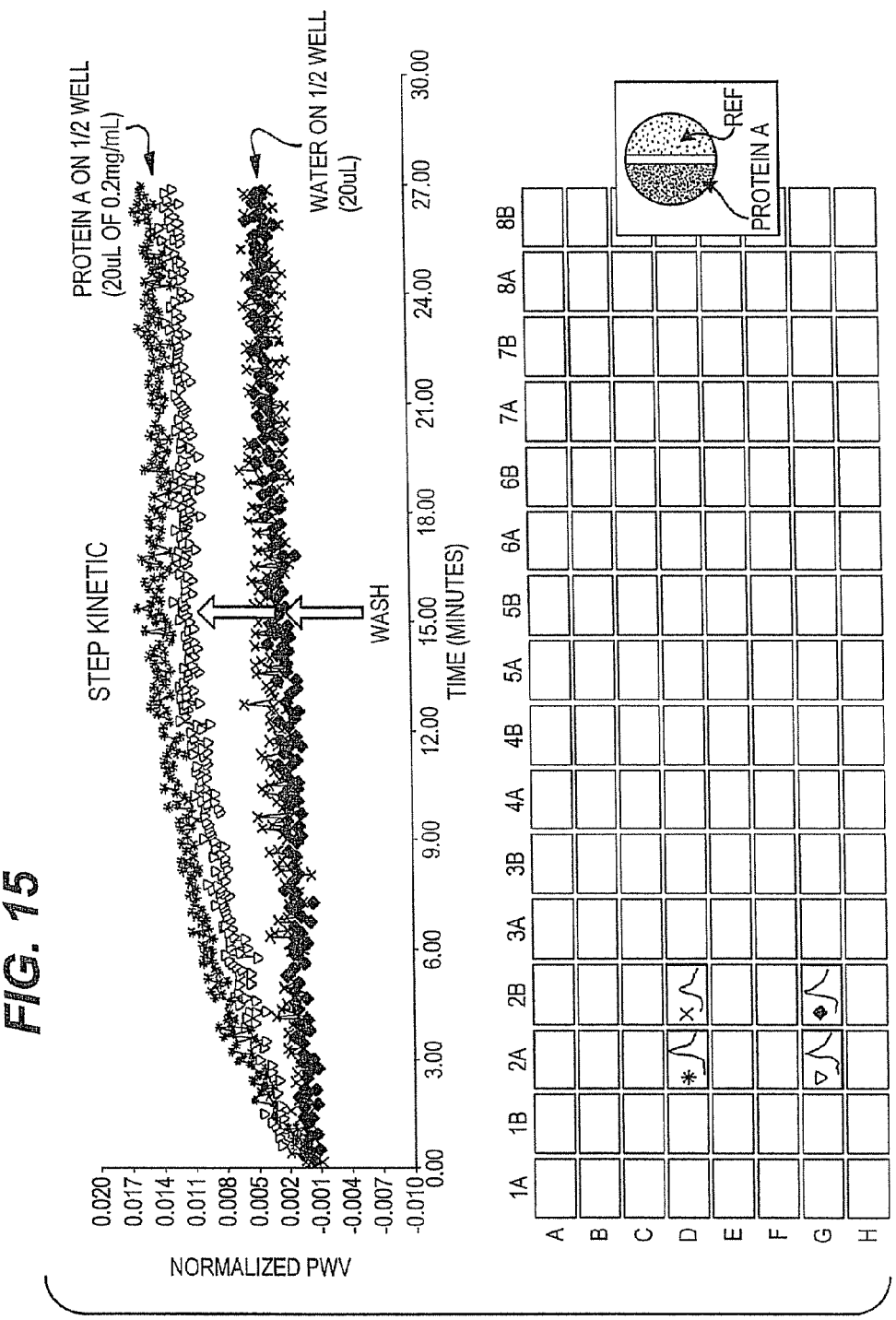
FIG. 15 shows protein A adsorption on ½ well. Protein A solution was added to the left half of the well while water was added to right half of the well. The peak wavelength shift was monitored over time. At 15 minutes the surfaces were washed with water.

Protein Adsorption. Under certain reaction conditions, Protein A can be non-specifically adsorbed to TiO creating a stable and functional surface. Protein A was adsorbed to ½ a well by adding 20 μL of a 0.2 mg/mL solution of Protein A in PBS; 20 μL water was added to the other ½ of the well. After 15 minutes of adsorption, solutions were removed and each side of the well was carefully washed with 3 exchanges of 20 μL water. Results are shown in FIG. 15. A shift of 0.1 nm is observed for protein A adsorption on ½ a well.

Figure 16:
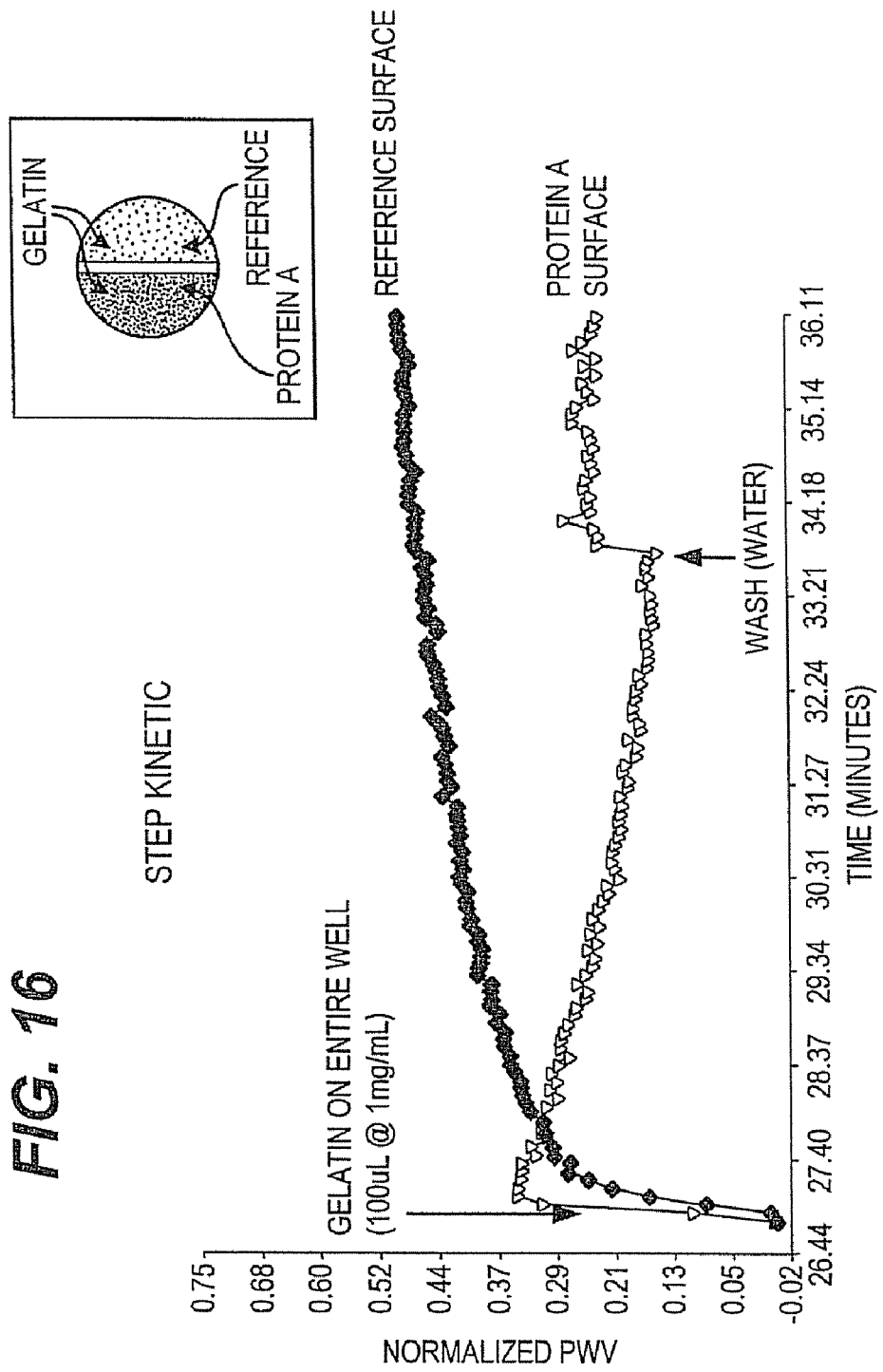
FIG. 16 shows surface blocking with gelatin. Gelatin was added to the entire well. After 10 minutes the wells were washed with 3 exchanges of water.

Gelatin Blocking Gelatin has a high affinity for TiO and adsorbs primarily to the 'naked' reference surface and fills in any bare TiO regions on the Protein A coated surface. All solution was removed from the wells and 100 μL of a 1 mg/mL gelatin solution was added to the entire well. Blocking was monitored by BIND and results are shown in FIG. 16.

Figure 17:
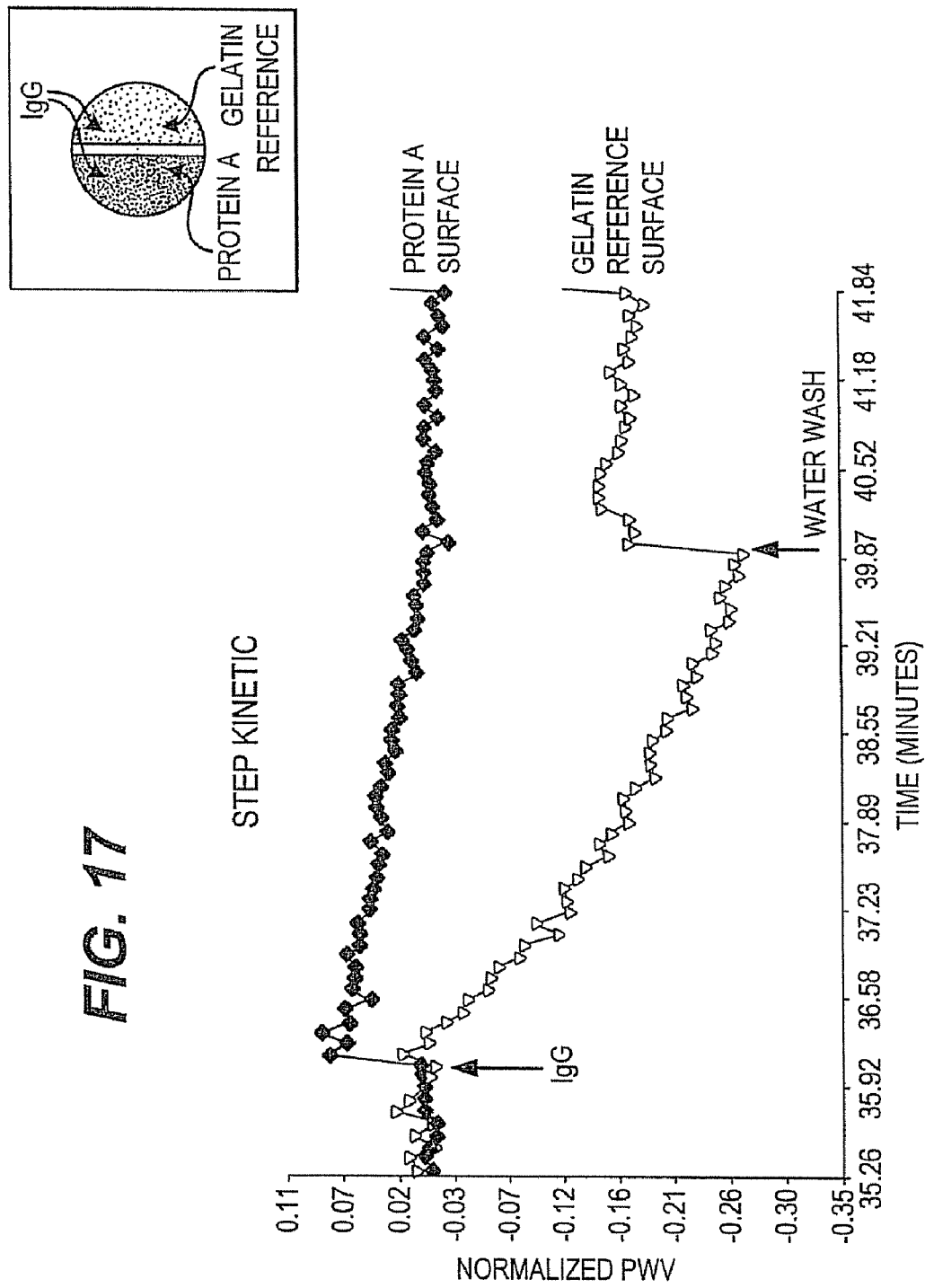
FIG. 17 shows a negative control. Goat IgG was added to the entire well. Very little, if any, IgG binding to either protein A or gelatin was observed. A reduction in signal is observed on the gelatin surface suggesting some material may be washing off the surface due to the change in buffer conditions.

Negative Control. Goat IgG binds weakly to protein A and was used in this experiment as a negative control. Goat IgG was diluted ⅟10 into wells containing water to a final concentration of 0.1 mg/mL. Results are shown in FIG. 17. As expected, no goat IgG is observed binding to either the protein A or gelatin reference surface. Because Protein A is adsorbed and not covalently bound to surface, some washing off is observed (as indicated by the decrease in signal) when the IgG solution is added because the solution contains salt.

Figure 18:
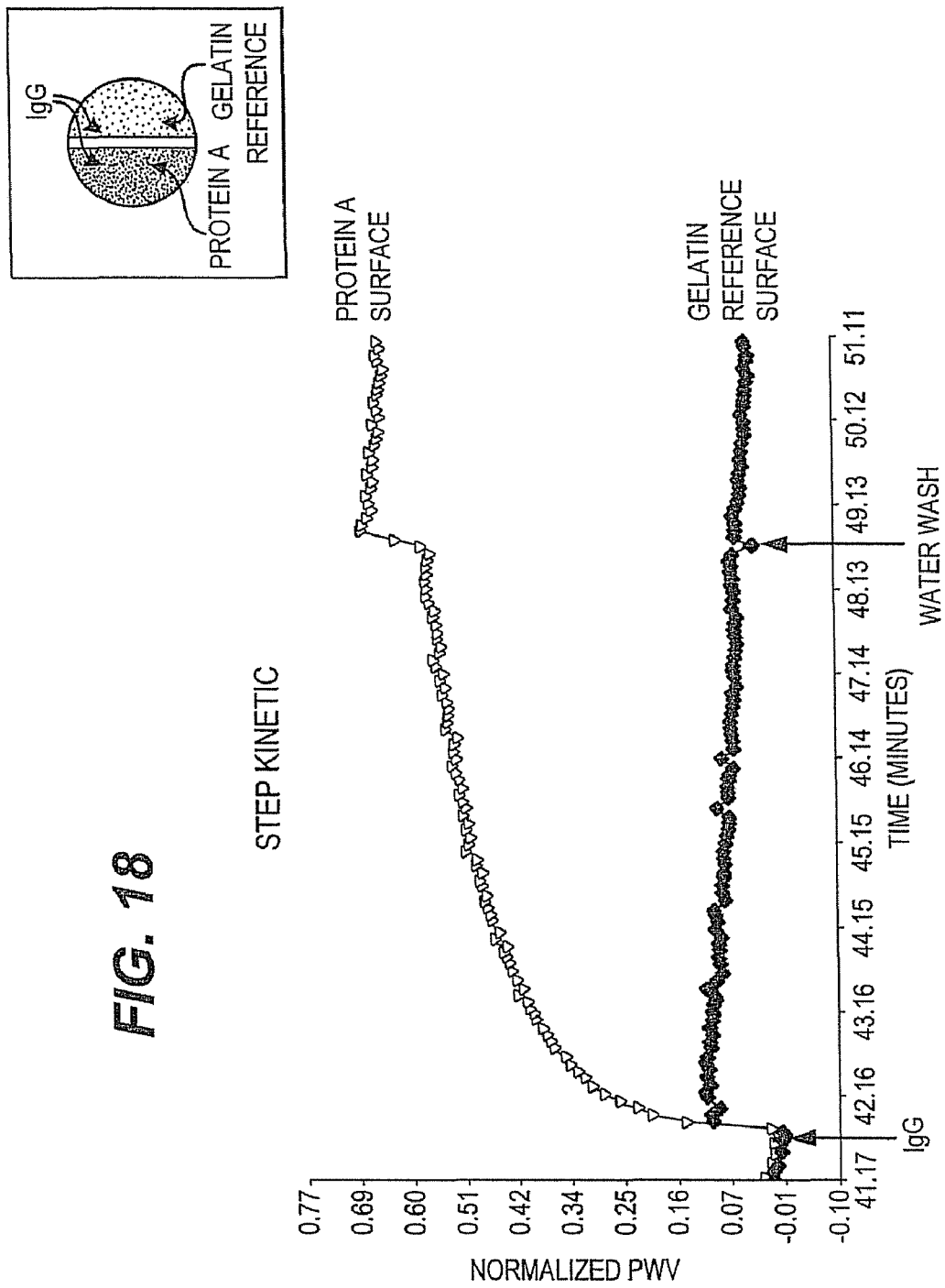
FIG. 18 shows a positive Control. Human IgG was added to the entire well. Specific binding to the Protein A surface is observed, while no binding is observed to the gelatin reference surface.

Positive Control. Human IgG binds strongly to protein A and was used in this experiment as a positive control. Human IgG was diluted ⅟10 into wells containing water to a final concentration of 0.1 mg/mL. Results are shown in FIG. 18. As expected, human IgG is observed binding to the protein A surface but not the gelatin reference surface.

Example 5

Experiment Setup

Plate—96-well biosensor microplate with a central line of UV curable adhesive drawn in the wells by an automated liquid dispensing instrument.

Instrument Setup—Instrument was set up to read 2 spots per well. Each spot was offset from the well center by +2 mm.

HSA—Warfarin Binding—HSA was covalently attached to sensor surface on the left side of the well. The right side of the well was an HSA-free reference surface to control for bulk shift and non-specific binding artifacts.

Initial reading. An initial measurement was made to observe the baseline peak wavelength shift over time in the neat wells. Each well contained 90 μL PBS and was read on each side of the barrier. Baseline drift measurements and peak shape/height read on either side of the well are equivalent.

HSA Immobilization. HSA was covalently immobilized on the left side of the well. Briefly, the left side of the well was activated for 3 minutes using 15 μL of standard amine coupling reagents and 15 μL HSA was added. Data are reported in FIG. 19.

Figure 19:
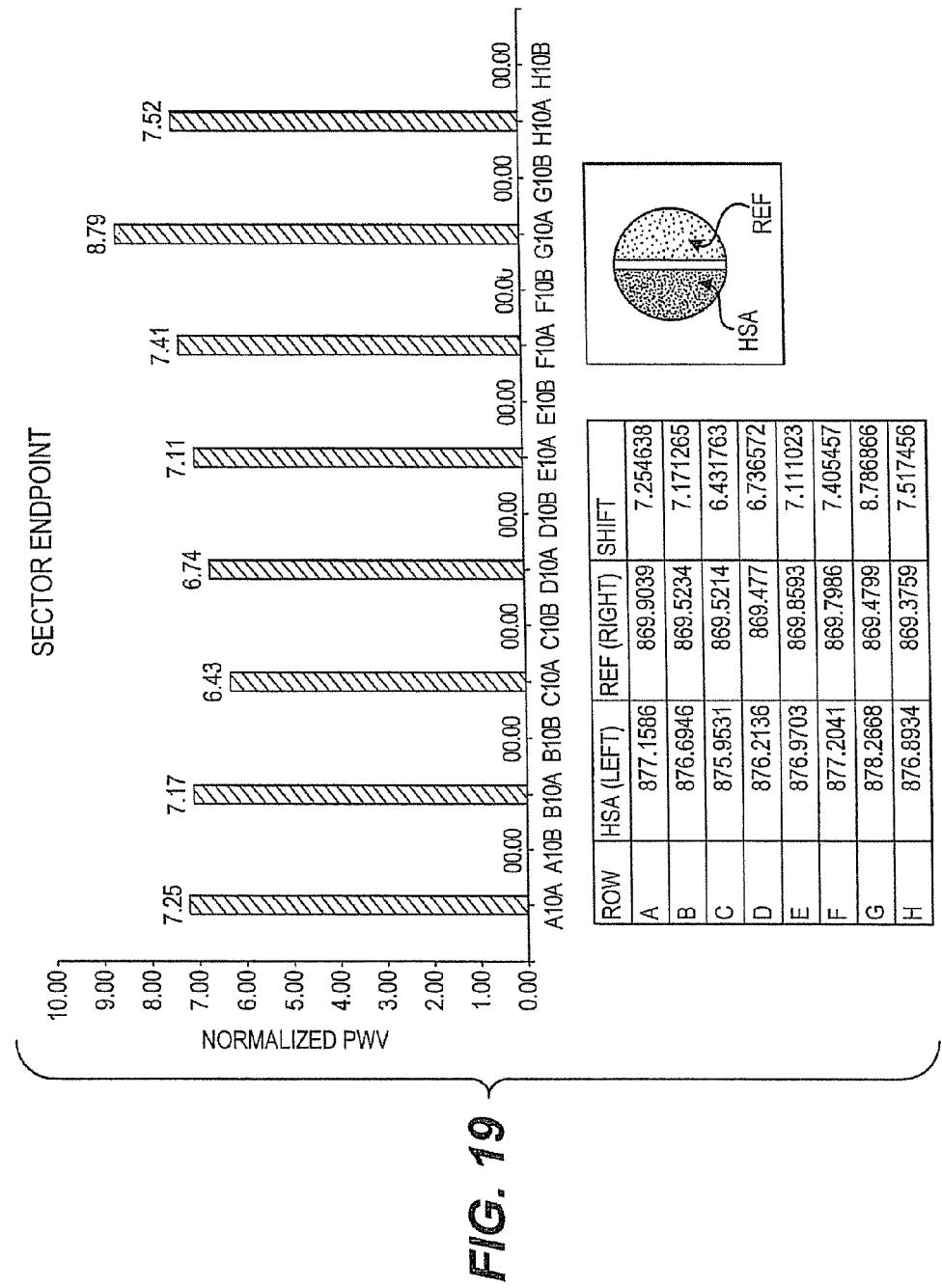
FIG. 19 shows split well HSA immobilization values for column 10. The left side of the well is coated with HSA (Ex. A10A) where as the right side of the well is blocked and used as a reference surface (Ex. A10B). The table shows the final PWV shift for the immobilized HSA.

Reference Surface. The right side of the well was used as a reference surface. The right side of the well was activated for 3 minutes using 15 μL of standard amine coupling reagents and 100 μL of 1M ethanolamine pH 8.5 was added to the whole well to block the surface. Results for HSA and reference surface are shown in FIG. 19.

Figure 20:
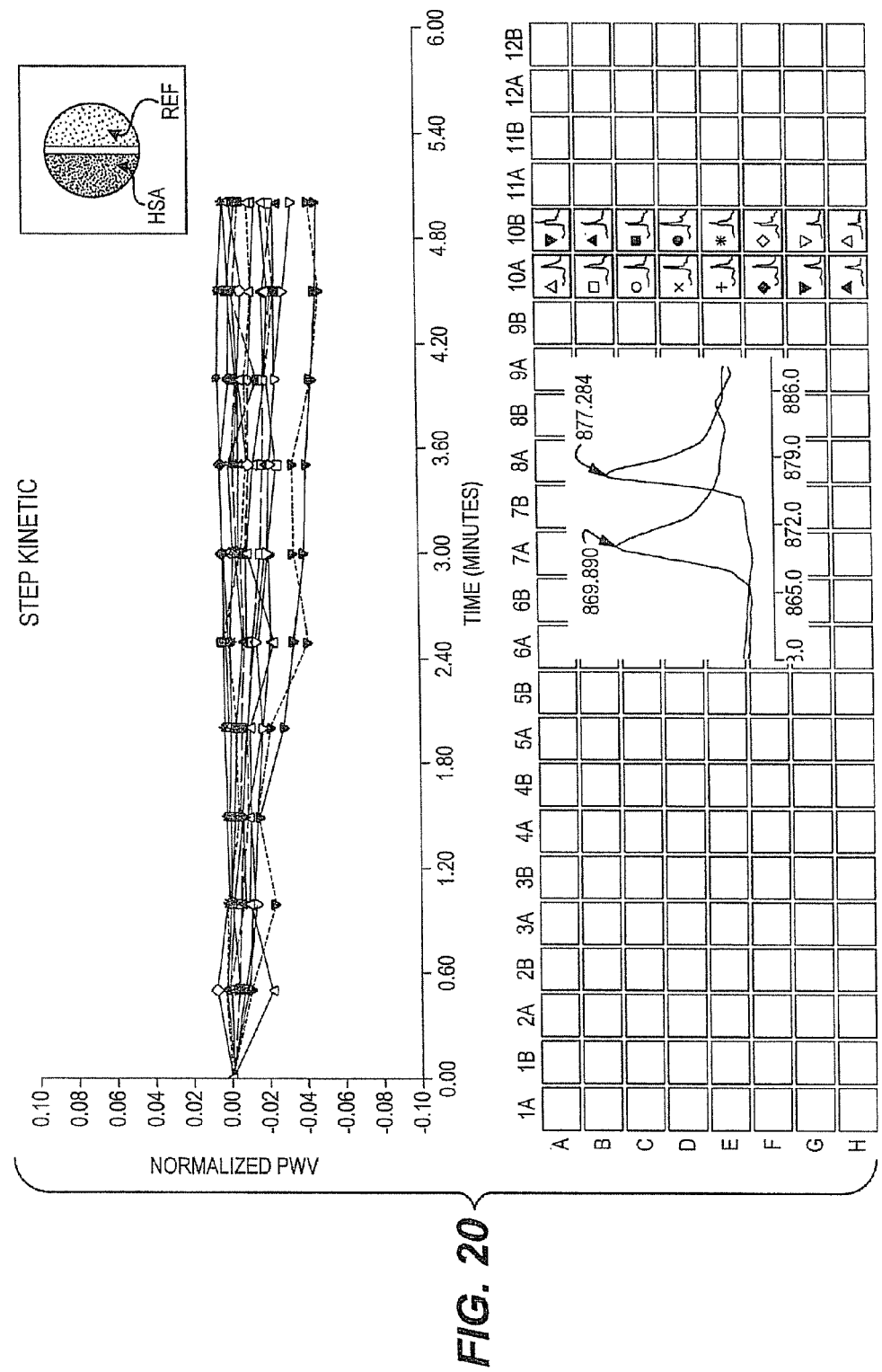
FIG. 20 shows split-well baseline reading. 90 μL of PBS+ 1% DMSO was added to the wells of column 10. Data was collected over time in 'self-referencing mode.' Inset shows representative overlaid spectra for the left and right sides of a well.

HSA Baseline. A pre-binding baseline was acquired with 90 μL of PBS+1% DMSO in the wells. The results from this baseline are shown in FIG. 20. The inset clearly shows the difference in PWV location for the left and right side of the well resulting from HSA immobilization specific to the left side of the well.

Figure 21:
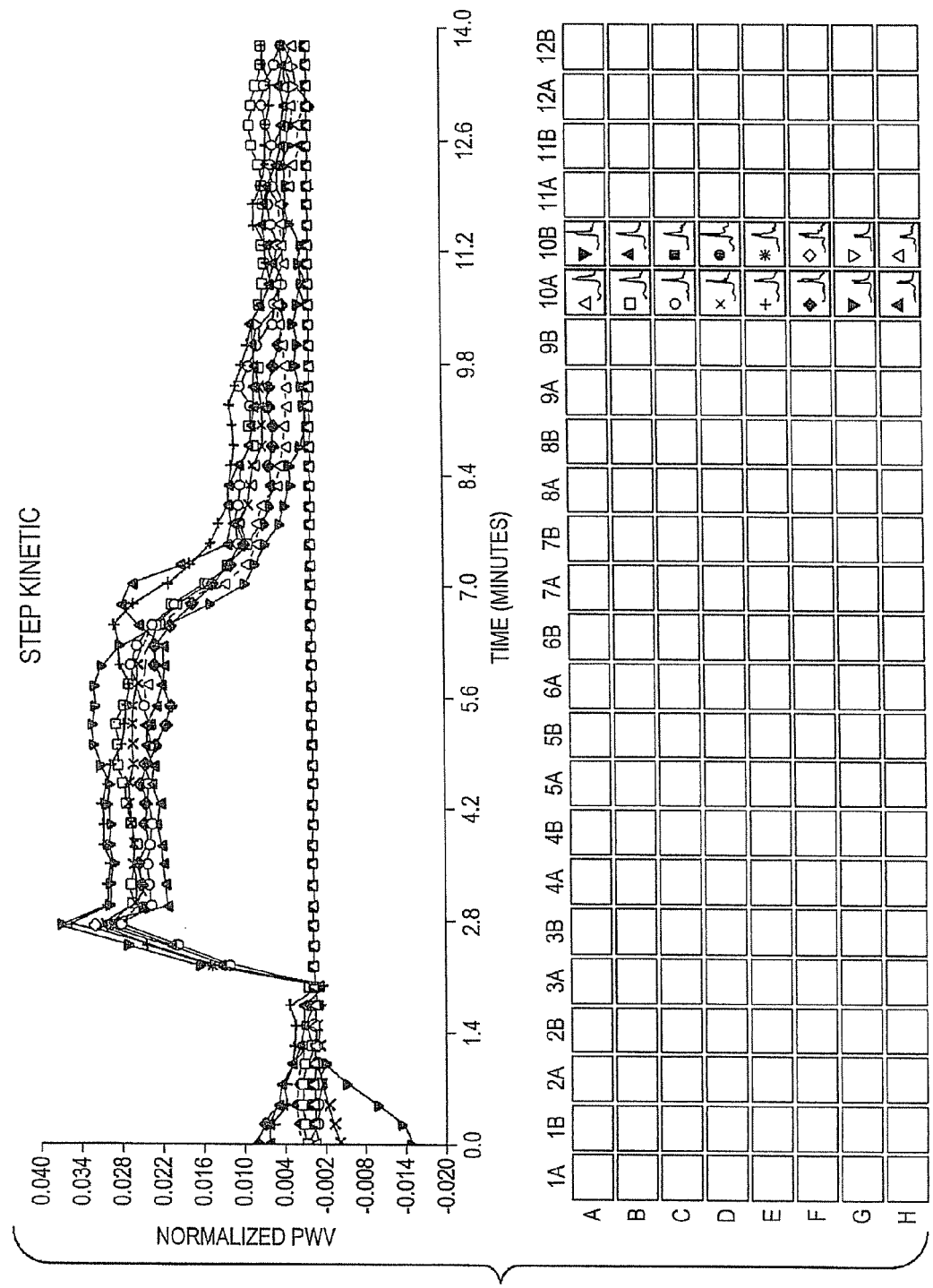
FIG. 21 shows split-well warfarin binding reading. Each well contained 90 μL of PBS+1% DMSO to begin the step. To this 10 μL of 500 uM warfarin was added and mixed, a final concentration of 50 μM is achieved. The response measured on the reference surface (resulting from bulk refractive index changes and non-specific binding) has been subtracted from the HSA surface in each well respectively.
Figure 22:
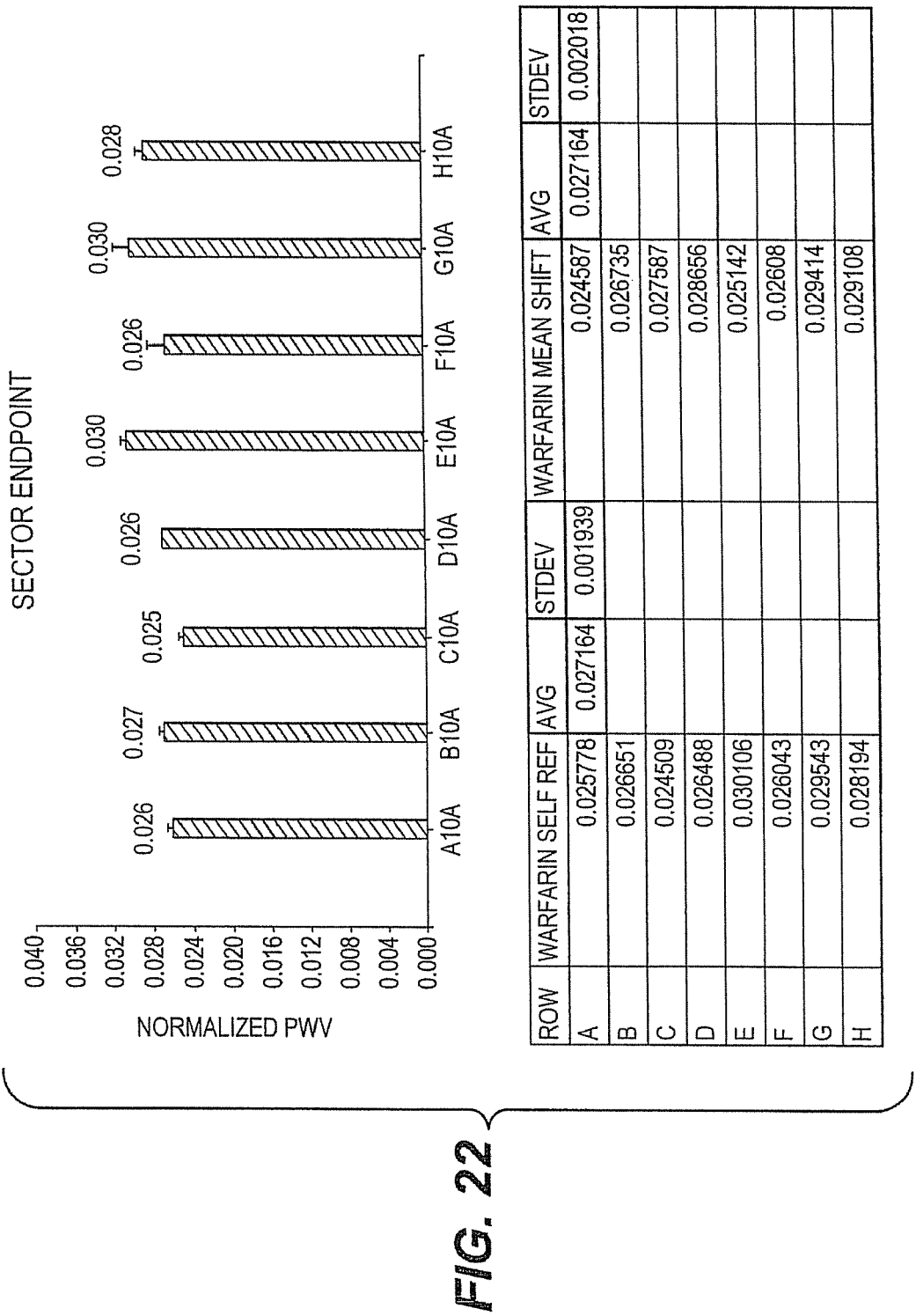
FIG. 22 shows endpoint values for Warfarin shift are shown, 'self referenced' vs. 'mean referenced'. The average response and standard deviation are shown for both methods of calculation. Endpoint is taken at kinetic point 15.

Warfarin Binding. An initial baseline is acquired with 90 μL of PBS+1% DMSO in the wells. To this solution 10 μL of 500 μM warfarin in PBS+1% DMSO is added and mixed. The final concentration is 50 μM warfarin in the well. Binding is allowed to continue for 4 minutes and wells are washed with PBS+1% DMSO. Results for warfarin binding are shown in FIG. 21. FIG. 22 shows a comparison of the warfarin binding data self-referenced versus referenced to an average of the reference surfaces. Self-referencing reduces the error in the measurement as observed by the reduction in standard deviation.

We claim:

1. A method of making a self-referencing colorimetric resonant optical biosensor comprising:
   (a) immobilizing one or more specific binding substances in an immobilization volume to one or more assay regions of a self-referencing colorimetric resonant optical biosensor, wherein the biosensor comprises a liquid holding vessel comprising a colorimetric resonant optical biosensor as a surface, and a fluid-impermeable divider on the colorimetric resonant optical biosensor surface, wherein the fluid impermeable divider separates the liquid holding vessel into two or more assay regions, wherein the fluid-impermeable divider segregates an immobilization volume within each assay region, and wherein the fluid-impermeable divider allows a reaction volume to encompass all assay regions in the liquid-holding vessel; and
   (b) preserving one or more assay regions as one or more reference regions, wherein the one or more reference regions do not contain immobilized specific binding substances.

2. The method of claim 1, wherein when the biosensor is illuminated a resonant grating effect is produced on the reflected radiation spectrum and wherein the depth and period of a grating of the biosensor are less than a wavelength of the resonant grating effect.

3. The method of claim 1, wherein a narrow band of optical wavelengths is reflected from the biosensor when the biosensor is illuminated with a broad band of optical wavelengths.

4. The method of claim 1, wherein the liquid-holding vessel is selected from the group consisting of a microtiter plate well, a test tube, a Petri dish and a microfluidic channel.

5. The method of claim 1, wherein the biosensor comprises two or more liquid-holding vessels.

* * * * *